(12) United States Patent
Saalasti et al.

(10) Patent No.: US 8,052,580 B2
(45) Date of Patent: Nov. 8, 2011

(54) METHOD AND SYSTEM FOR GUIDING A PERSON IN PHYSICAL EXERCISE

(75) Inventors: Sami Saalasti, Jyväskylä (FI); Aki Pulkkinen, Tikkakoski (FI); Joni Kettunen, Säynätsalo (FI); Mikko Seppänen, Posio (FI)

(73) Assignee: Firstbeat Technologies OY, Jyvaskyla (FI)

( * ) Notice: Subject to any disclaimer, the term of this patent is extended or adjusted under 35 U.S.C. 154(b) by 0 days.

(21) Appl. No.: 12/308,384

(22) PCT Filed: Jul. 4, 2007

(86) PCT No.: PCT/FI2007/050411
§ 371 (c)(1),
(2), (4) Date: Dec. 12, 2008

(87) PCT Pub. No.: WO2008/003830
PCT Pub. Date: Jan. 10, 2008

(65) Prior Publication Data
US 2010/0216601 A1    Aug. 26, 2010

(30) Foreign Application Priority Data

Jul. 4, 2006   (FI) .................................. 20065475
Jul. 4, 2006   (FI) .................................. 20065476

(51) Int. Cl.
*A63B 71/00*    (2006.01)

(52) U.S. Cl. ..................................... 482/8; 482/1; 482/9

(58) Field of Classification Search ................. 482/1–9, 482/900–902; 434/247, 254, 255; 600/587, 600/595
See application file for complete search history.

(56) References Cited

U.S. PATENT DOCUMENTS

| | | | | |
|---|---|---|---|---|
| 5,318,487 A | * | 6/1994 | Golen et al. | 482/5 |
| 5,476,427 A | * | 12/1995 | Fujima | 482/3 |
| 5,478,295 A | * | 12/1995 | Fracchia | 482/7 |
| 5,526,290 A | * | 6/1996 | Kanzaki | 702/160 |
| 5,527,239 A | * | 6/1996 | Abbondanza | 482/8 |
| 5,769,755 A | * | 6/1998 | Henry et al. | 482/8 |
| 5,879,270 A | * | 3/1999 | Huish et al. | 482/8 |

(Continued)

FOREIGN PATENT DOCUMENTS

FI    113614    5/2004

(Continued)

*Primary Examiner* — Loan Thanh
*Assistant Examiner* — Sundhara M Ganesan
(74) *Attorney, Agent, or Firm* — Fildes & Outland, P.C.

(57) ABSTRACT

The invention relates to a method and system for guiding a person to a physiological cumulative state in physical exercise, in which the exercise has a physiological target in the form of a physiological state at the end of the exercise, a duration, and a performance parameter. In the method at the start of the exercise the physiological target is set, as is the value of the performance parameter, and during the exercise at regular intervals: at least one quantity proportional to the momentary intensity is measured, and the present physiological state and an estimate of the physiological state and the end of the exercise are calculated with the aid of the momentary intensity and the exercise performed, and a guidance range for the momentary intensity is defined, in order to reach the target state and the performance parameter. The user is guided by means of feedback to remain within the said guidance intensity range. At the start of the exercise the intensity guidance range is expanded according to a pre-selected function, in order to reduce the variation in the guidance.

3 Claims, 15 Drawing Sheets

U.S. PATENT DOCUMENTS

| | | | | |
|---|---|---|---|---|
| 6,002,982 A * | 12/1999 | Fry | | 701/213 |
| 6,013,007 A * | 1/2000 | Root et al. | | 482/8 |
| 6,013,008 A * | 1/2000 | Fukushima | | 482/8 |
| 6,605,044 B2 * | 8/2003 | Bimbaum | | 600/500 |
| 6,837,827 B1 * | 1/2005 | Lee et al. | | 482/8 |
| 7,402,125 B2 * | 7/2008 | Wang | | 482/1 |
| 7,572,205 B1 * | 8/2009 | Cribar | | 482/3 |
| 7,601,098 B1 * | 10/2009 | Lee et al. | | 482/8 |
| 7,670,263 B2 * | 3/2010 | Ellis et al. | | 482/8 |
| 2004/0043869 A1 * | 3/2004 | Sato et al. | | 482/8 |
| 2004/0077462 A1 * | 4/2004 | Brown et al. | | 482/8 |
| 2005/0288154 A1 * | 12/2005 | Lee et al. | | 482/3 |
| 2006/0032315 A1 * | 2/2006 | Saalastic et al. | | 73/808 |
| 2006/0154713 A1 * | 7/2006 | Sunazuka et al. | | 463/6 |
| 2006/0217231 A1 * | 9/2006 | Parks et al. | | 482/3 |
| 2009/0005220 A1 * | 1/2009 | Lee et al. | | 482/8 |
| 2009/0069156 A1 * | 3/2009 | Kurunmaki et al. | | 482/9 |
| 2010/0056341 A1 * | 3/2010 | Ellis et al. | | 482/9 |

FOREIGN PATENT DOCUMENTS

WO     2005/031272     4/2005

* cited by examiner

Target distance/
target position at the
end of exercise

METHOD AND SYSTEM FOR GUIDING A PERSON IN PHYSICAL EXERCISE

BACKGROUND TO THE INVENTION

1. Field of the Invention

The field of the invention is the improvement of physical fitness in sport and exercise and the improvement of the state of health. The invention is intended to guide a sportsperson or an exercise enthusiast to a physiological target state defined prior to exercise, in a desired time, over a desired distance, or over a desired route. The invention can relate to applications relating to improving in fitness, health, and relating to weight management. More specifically, the invention relates to what is stated in the preamble to Claim 1. The invention also relates to a corresponding system.

In physical exercise, there is usually not only a physiological target state, but also a performance parameter, which is either the duration or distance of the exercise. Thus the exerciser makes, for example, a workout of 60 minutes, when the duration of the exercise has been fixed. Another usual form of physical exercise is a loop over a set distance. The exerciser will often have a familiar route, over which they run. In that case, the distance is fixed. However, the most important parameter is the physical training effect, which is determined on the basis of the cumulative physiological target state. The physiological state is calculated with the aid of a suitable physiological quantity.

2. Description of the Related Art

Previous attempts have been made to guide exercise by means of methods that are difficult for the user. Previously, methods have been based, for instance, on rigid intensity limits (heart-rate range), to which the exercise is guided. Thus, the heart-rate range is not altered to take into account deviations occurring during exercise (e.g., being above or below the heart-rate range for long periods of time). In addition, diverse, improvement-oriented training requires more complex decision criteria, which are affected by, for instance, the desired duration of training and the training intensity/training induced stress.

Particularly when guiding exercise towards a specific target value of a cumulative quantity, more comprehensive operation is demanded from the guidance system. A more comprehensive guide system is required, because, when predicting the value of a variable farther into the future, even a small change in intensity at the present moment, or in the slope of a cumulative variable will lead to a great change after 30 minutes, for example. This means that the intensity range, to which the target is guided, becomes very narrow. It is very difficult to train on the basis of the feedback based on such a narrow intensity range. By itself, the tolerance of the intensity range (for example, averaging in a selected time window) will not help to solve this problem.

Patent publication FI 115288 discloses a method, in which the heart rate is kept below a specific threshold during post-exercise cool down. The method is based, however, on defining only a specific heart-rate level and on guiding cooling down on the basis of this heart-rate level, and thus does not, in this aspect, differ essentially from other exercise guidance methods based on heart rate level. The patent in question describes a specific blood lactate level (physiological target state), after which the cooling down can be stopped. The system described lacks dynamic guidance relative to a pre-defined target time or target distance.

Patent application US2005/0026750 discloses a control system for a treadmill. The system is based on predefined speeds. The user is informed if they exceed or do not reach heart-rate limits. Final cool down can be stopped once the heart rate has dropped to the desired percentage of the maximum level. The application disclosed is based on rigid heart-rate limits, which does not take into account exercise that may differ from the guidance at the start of the exercise.

Patent publication U.S. Pat. No. 6,304,774 discloses a method, in which the resistance of an exercise device is controlled on the basis of a collected heart-rate signal and, for example, on cadence. The control is, however, based only on heart-rate limits, and deviations from the target intensity are not permitted.

Patent publication U.S. Pat. No. 6,605,044 discloses a device, utilizing heart rate, measuring energy consumption with the aid of a calculation algorithm, in which a target for the exercise can be set, and a method for monitoring the achievement of the exercise target. The target set for the person can be either the amount of energy consumed, or a reduction in weight. In the invention, in addition to the heart rate during the exercise, both the momentary and cumulative energy consumption and, the accumulated energy consumption during several exercises, the number of calories, which must still be consumed for the target to be achieved, are displayed, as well as the time required to achieve the target at the present intensity. Even though physiological targets (amount of energy consumed, or weight reduction) can be set in the invention, it differs from the system depicted in the present application, because publication U.S. Pat. No. 6,605,044 does not describe any sort of guidance method that guides the user to the target. In the invention, it is not even possible to set a target time or other corresponding criterion for the performance, on the basis of which it would be possible to guide the performance. In addition, basing the guidance of the exercise on the time taken to achieve the predicted target on the basis of the present intensity leads to a situation in which a small change in the present intensity will cause, when predicting farther into the future, a change in the cumulative physiological variable (or in any other variable whatever, for instance, in the distance), so that in practice it will be very difficult, if not impossible to guide the exercise towards the target on the basis of this feedback.

Firstbeat Technologies Oy's patent application US2006/0032315 (Saalasti et el.) 'METHOD FOR MONITORING ACCUMULATED BODY FATIGUE FOR DETERMINING RECOVERY DURING EXERCISE OR ACTIVITY' discloses a method for calculating a stress index. The index can also be EPOC (Excess post-exercise oxygen consumption). The patent application does not, however, disclose a method for guiding a person to a physiological target.

Firstbeat Technologies Oy's patent application US2006/004266 'SYSTEM FOR MONITORING AND PREDICTING PHYSIOLOGICAL STATE UNDER PHYSICAL EXERCISE' discloses a system, whish predicts the time for achieving a target.

Patent publication U.S. Pat. No. 5,478,295 discloses a method, which seeks to provide feedback to someone performing exercise, which will assist the user in reaching a target that one has set, or in motivating him/her to continue exercise after having already reached a target.

If the user decides to carry out exercise with a specific temporal duration, this will also set a suitable (virtual) distance target for the exercise. The exercise terminates when the predefined temporal duration terminates. This combination of time and distance is such that the user can use it to estimate a suitable exercise heart rate. During the exercise, the speed required to achieve the distance target and the predicted result of the exercise (prediction of the distance traveled once the target time has ended) are displayed to the user. The user takes his/her pulse themselves and presses a button on the computer on every third heart beat. The computer can calculate the user's heart rate from this and displays it to the user. If the heart rate is not in the desired range, the user can select a more suitable time-distance pair in the next exercise session. During exercise, the user can compare, by himself/herself, his/her present speed with the target speed and the distance target from the predicted result (prediction of the distance traveled when the target time ends). In addition, according to the invention, the user can be shown whether the predicted result of the exercise is equal to, greater than, or less than the target distance. On the basis of these data, the user can aim at either the precise target, or even at exceeding it. Once the distance target has been reached, the user can use the predicted result to motivate oneself for the remaining time.

If the user decides to perform a workout, for which there is a (virtual) target distance, this will also set a suitable time target for the workout. The workout will end once the predefined distance has been traveled. The user estimates that by using this combination of distance and time he/she will achieve a suitable exercise heart rate. During the exercise, the user is shown the speed required to reach the time target and the predicted result of the workout (prediction of the final time once the target distance has been traveled). The user takes his/her own pulse and presses a button on the computer on every third heart beat. The computer can calculate the user's heart rate from this and display it to the user. In the next workout, the user can select a more suitable time-distance pair, if the heart rate is not in the desired range. During the workout, the user himself/herself can compare his/her present speed with the target speed and the time target from the predicted result (prediction to the final time once the target distance has been completed). In addition, according to the publication, the user can be shown whether the predicted result of the workout is equal to, greater than, or less than the target time. On the basis of these data, the user can aim at either the precise target time, or at less than it. If the target time is exceeded, the user can nevertheless aim at the best possible result, using the predicted final time as motivation.

Patent publication U.S. Pat. No. 5,478,295 does not, however, disclose the use of a cumulative physiological target state, nor is it even easy for the user to evaluate the physiological effect of the workout. The same time-distance pair can be performed using different intensity profiles, which achieve quite different physiological effects. According to the publication, impossible speeds are not recommended to the user, but the publication fails to depict any principle on the basis of which impossible target speeds can be excluded.

The whole time, the user must watch the numerical feedback given. In particular, aiming at a specific physiological state (heart-rate range) is left to be the responsibility of the user. Thus, the method disclosed in patent publication U.S. Pat. No. 5,478,295 does not solve the problem of how to provide the user with sensible feedback during exercise, which feedback would guide the user to a physiological target state within the framework of a target time or target distance/ route. User-friendly guidance, such as would be suitable for exercise combining a target-distance/target time pair, is also not depicted. The principle of expansion (broadening) of the guidance range, which is a property essential for user-friendliness, is also entirely missing from the publication. In addition, patent publication U.S. Pat. No. 5,478,295 entirely lacks visual and auditive feedback, displayed and repeated to the user at a suitable frequency, even though it is essential for user friendliness.

Firstbeat Technologies Oy's patent application US2006/ 004265 'SYSTEM FOR MONITORING AND PREDICTING PHYSIOLOGICAL STATE UNDER PHYSICAL EXERCISE' discloses a system for monitoring a physiological state during exercise and predicting the physiological state at the end of a workout. The system disclosed in the application predicts the time taken to achieve the target, but does not guide the user to the target and gives the user no instructions as to how to act at a specific moment in a workout. The publication presents a cumulative quantity, which is suitable when monitoring the cumulative stress of physical exercise. For example, energy consumption by itself is a poorer indicator, because energy is consumed even without physical stress, and energy consumption is not directly connected to homeostatic changes taking place in the body.

SUMMARY

The present invention is intended to create a method and system, which guides a person dynamically to a predefined physiological target state using a selected performance parameter, which is the predefined duration or distance of the exercise, or the selected route. The characteristic features of the method according to the invention are stated in the accompanying Claims. The method according to the invention operates dynamically by guiding the exercise towards the target even if the set criteria have not been followed earlier in the course of the exercise. The method works in all conditions, both in steady-pace and in interval-type exercise, independently of the duration of the exercise.

In one embodiment, the lower limit of the expanded guidance range of the intensity is defined in such a way that, at the defined performance ability of the person, the workout can, at each moment, still be completed, in such a way that the physiological or distance target will be reached in the target time.

In one embodiment, the cumulative target state is calculated using some physiologically cumulative quantity, which is proportional to the change in general homeostatic state achieved by exercising, together with its change, for example, using the EPOC value.

The values of the target state and/or of the performance parameter are preferably defined together with their tolerances. This gives the exercise some degree of freedom, at both the beginning and end of the workout. The physiological justification for this is that the intended physiological effect will be achieved, even though these values deviate to some extent from the intended values. Thus, instead of intended 30-minute duration, the real duration of the exercise can be 25-35 minutes. Alternatively, the real training effect can vary within small limits, which will make the guiding of the exercise more comfortable for the user.

Dynamic exercise guidance is formed of the variables used, i.e. the target, the target time, possibly the target distance and/or route, as well as their guidance criteria. In this case, the term guidance criteria refers to the time elapsed and the physiological state of the person, or, for example, the external power, on the basis of which the person is guided towards the set target. In addition, the system includes methods for creating real-time information for the user, for expanding the targets, and for the actual guidance of the exercise. The controlled expansion of the targets permits the measured physiological variables to deviate from the guidance criteria, for example, in terrain, when the intensity or speed may vary considerably, in which case the smart system can permit short (or long) deviations from the guidance criteria, while the physiological target state is nevertheless achieved within the set target time.

The variation of the guidance criteria and the expansion of the target permits different types of exercise, as using only one criterium does not cover well different types of alternative exercise. For example, the use of only the heart-rate range will in principle guide steady-pace exercise, but not interval type. The guidance of the system described in the present invention is sufficiently sensitive to react rapidly to the criteria being significantly exceeded or not being reached.

The embodiments and devices of the invention include heart rate monitors or other devices measuring heart rate, personal digital assistance (PDA) devices, mobile telephones, mobile terminals, and other similar devices, which can be carried during exercise. The invention can be exploited not only to improve physical fitness, but also, for example, in stress management. Naturally, the functionalities can also be examined in a so-called offline state.

The system for the dynamic guidance of exercise described in the invention eliminates the drawbacks arising in previous inventions, i.e. it operates in all kinds of exercise, both steady pace and interval-types, irrespective of the duration of the exercise. The guidance system is sufficiently sensitive to react rapidly to speed that is too high or too low. Because the different ways of performing exercise are not, however, significant within certain limits in terms of achieving a physiological target state, the system permits exercise to be performed more freely without the system continually interfering with it. Conventional guidance systems based on heart-rate level, or other similar parameters do not permit this.

DETAILED DESCRIPTION OF THE INVENTION

The variables used in the invention can be grouped as follows:
1. Actual target (e.g., time, training effect 'TE', distance, cumulative energy consumption, amount of work (J), oxygen consumption (I), EPOC amount, heart-rate sum, training impulse (TRIMP), blood lactic acid concentration),
2. Guidance criteria for achieving the target, i.e. performance criterion, (e.g., speed, power output of work (W), EPOC change, accumulated EPOC, energy consumption (kcal/min), energy consumed (kcal), oxygen consumption (ml/kg/min), total oxygen consumption (I), heart-rate level, TRIMP already accumulated, number of steps, work output as a function of speed and inclination of surface, change in blood lactic acid concentration, etc.).

Different guidance criteria can also be used for the same target (e.g., conversion of energy consumption to (J), change or accumulation of EPOC to (I), so that the target can be stabilized, for example, and the guidance criteria converted. Naturally, the variables can be adapted to function the other way round as well.

The guidance criterion can also be dynamic, in which case different criteria are used at different stages of the exercise, which may occur, for example, in interval training. The target can be formed of several criteria, for example, a time-distance pair, in which case the natural guidance criterion would be, for example, speed. Some targets are bound to specific target criteria (and vice versa).

In one embodiment of the invention, there can be more than two targets.

Figure 1:
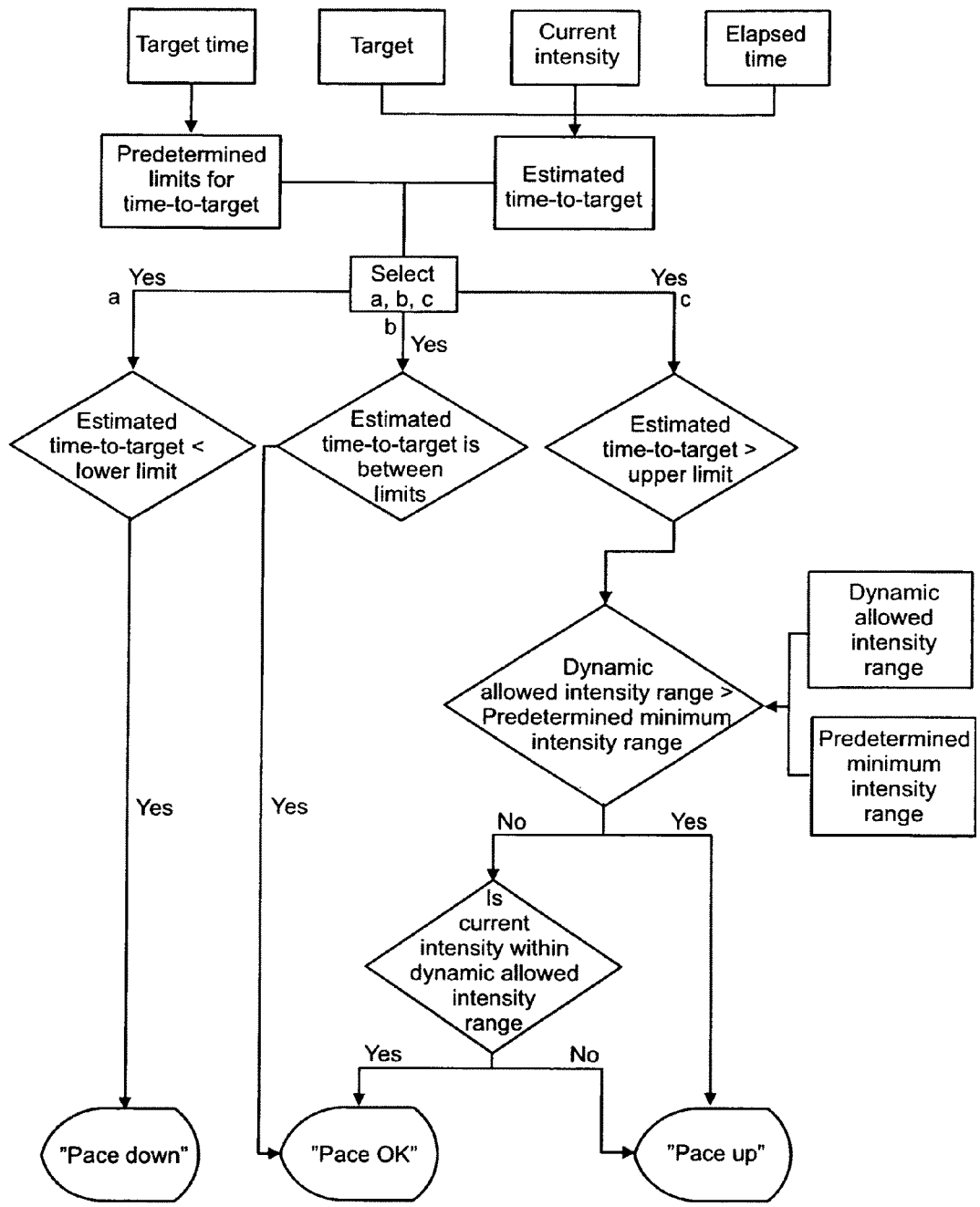
FIG. 1 shows the operation of the intensity limits and the time limits.

FIG. 1 shows the mutual operation of the intensity limits and time limits characteristic of the invention.

Figure 2:
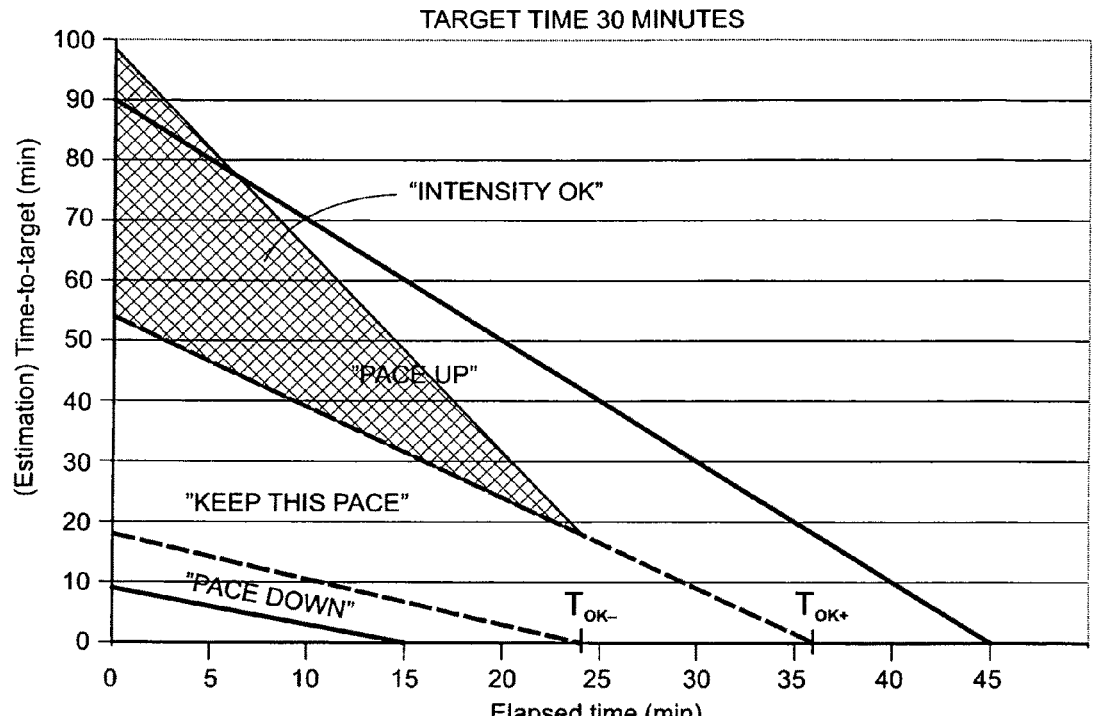
FIGS. 2 and 3 show possible embodiments of the invention for guiding exercise on the basis of a time-target performance parameter and an artificially expanded intensity range.
Figure 3:
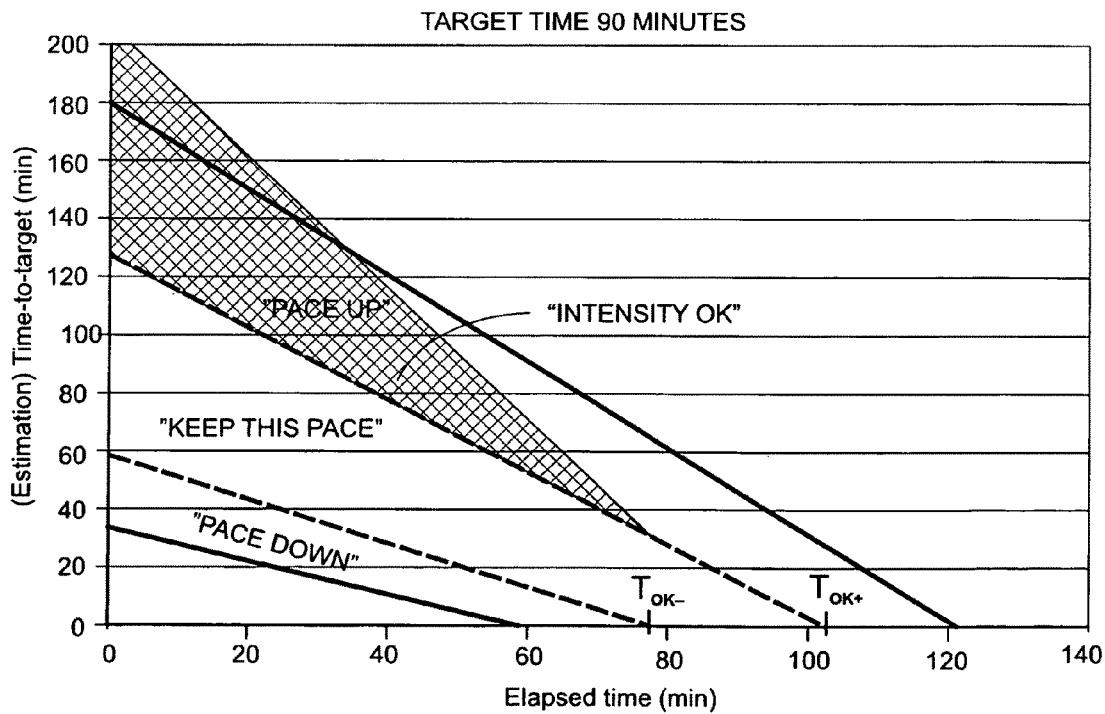

Examples of the predefined expert time limits for different distances of the target time, referred to in the diagram, ate shown in FIGS. 2 and 3 (Example 1). As the figures show, the target can be reached within a certain time window, and thus it is unnecessary to achieve precisely the target temporally. The lower limits 'Keep this pace' contain an empirically obtained small expansion, thus suiting people of all fitness levels. However, this is not sufficient for flexible guidance, instead the shaded zone 'Intensity OK' shows schematically the 'Max-30%' intensity expansion area described later, which will allow the person to still achieve the target, even though the intensity drops quite low, i.e. the time target escapes momentarily quite far. More reliable guidance will be achieved by means of the additional criteria according to FIGS. 16a and 16b, which are described later.

The aforementioned dynamic 'Intensity OK' zone is calculated as follows:

Parameters:
  Target=some cumulative quantity (referred to later in greater detail)
  Target time=the time in which it is wished to reach the target
  t_OK−=the earliest moment in time, when it is permitted to reach the target
  t_OK+=the latest moment in time, when it is permitted to reach the target
  minimum width of intensity=minimum intensity range permitted for the variation of the intensity
1. Calculate the intensity, at which the set target is reached at the t_OK− moment=OK− intensity.
2. Calculate the intensity, at which the set target is reached at the t_OK+ moment=OK+ a. The prediction in sections 1-2 is based both on the time already elapsed and on the target already accumulated, i.e. how long a time there is to t_OK− or t_OK+, and on how much the target should still accumulate in this time.
3. If the difference between the OK− intensity and the OK+ intensity is less than the set minimum width of intensity, this intensity range is expanded, in such a way that the intensity OK range is calculated as OK− intensity minus minimum width of intensity.
4. The intensity OK range becomes dynamic by always being examined at the desired moments in time and being dependent on how close the target have been approached.
5. A dynamic intensity range, which is however artificially expanded in the beginning of exercise, is required since otherwise the intensity range would be vanishingly narrow, particularly in a long workout.
6. The adjustment of the dynamic intensity range thus acts to artificially expand the range at both the start of the workout and also to dynamically update it during the workout, depending on whether the target state is approached more quickly or slowly than optimally. A pre-selected function reduces the artificial expansion to zero towards the end of the workout.

Figure 4A:
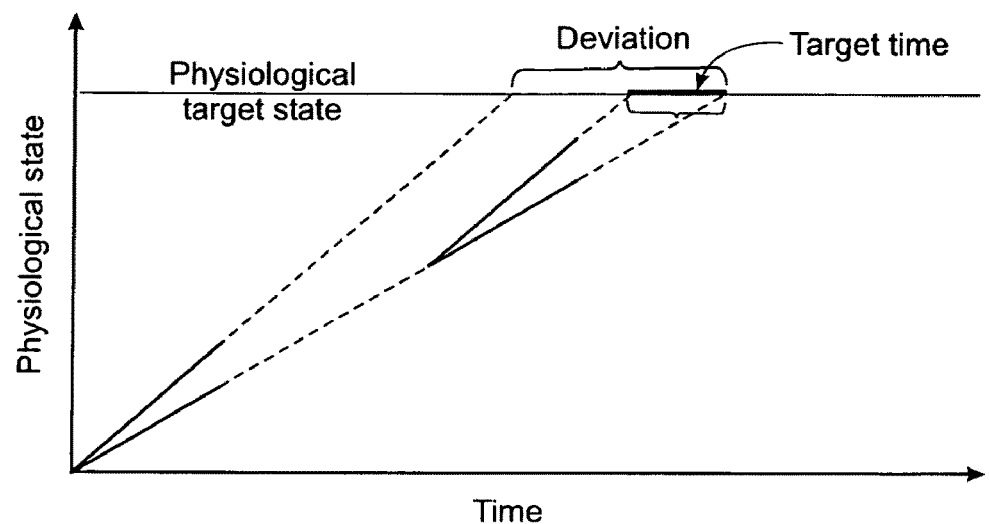
FIGS. 4a and 4b show the justification for the artificial expansion of the intensity range at the start of exercise.
Figure 4B:
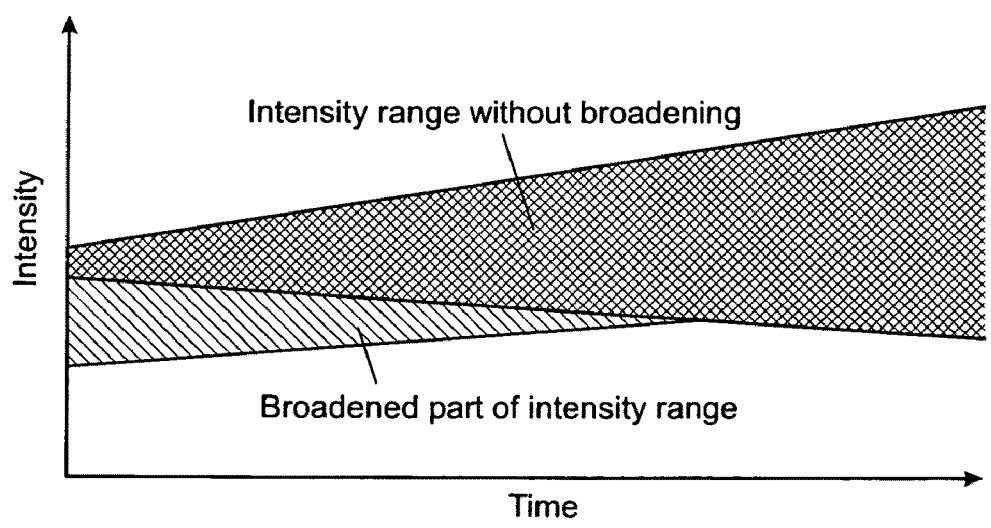

The need for a dynamic intensity range is justified in FIGS. 4a and 4b. A small change in intensity at the start of a workout will cause a large change in the time in which it is estimated that the physiological target will be reached ('deviation' FIG. 4a). Even though a small deviation would be to be permitted in the target time, the changes in intensity nevertheless generally predict that the target will not be reached within the scope of the deviation. When any workout progresses and the target time simultaneously approaches, a change of the same magnitude in intensity will no longer cause as great a difference in the predicted time for reaching the target. Before long, a situation will be reached in the latter half of the workout, in which the user can even vary the intensity very greatly, without the system attempting to correct the intensity. However, before reaching such a stage the intensity range must be expanded, to save the user from having to correct the intensity uncomfortably often (FIG. 4B). Expanding the permitted intensity range at the start of a workout thus permits the user to perform the workout and slightly vary the intensity, without the system continually commanding the user to correct the intensity.

Figure 16A:
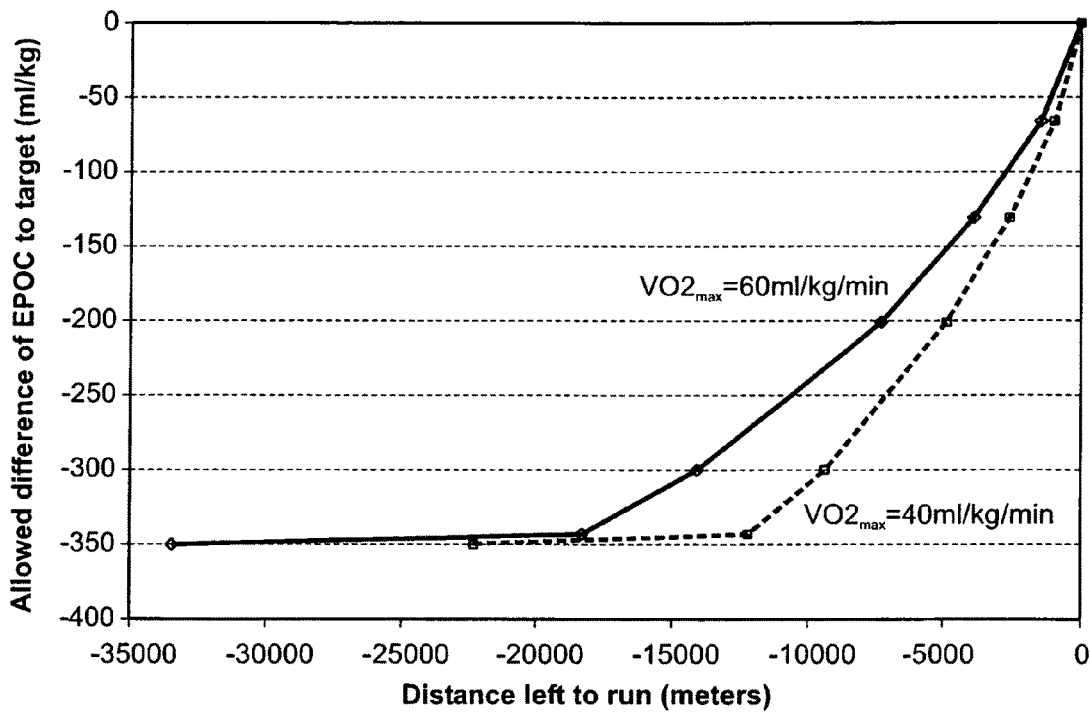
FIGS. 16a and 16b shows an example of lower-limit functions of intensity guidance.
Figure 16B:
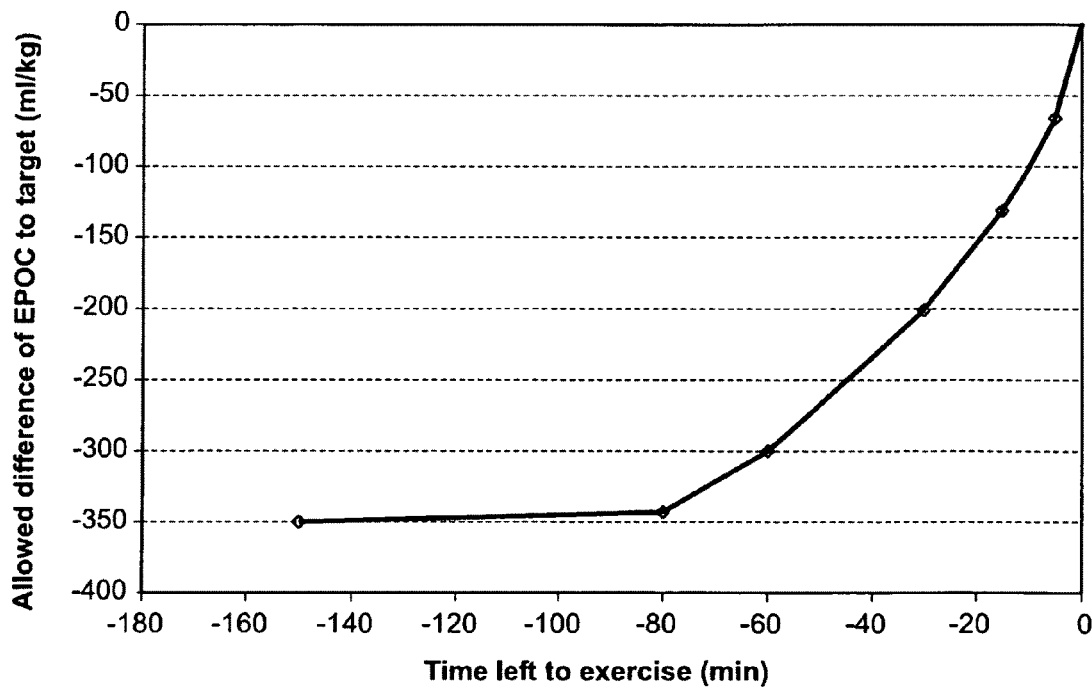

The limits shown in FIGS. 2, 3, and 4 and all the other limits relating to the dynamic guiding of exercise can also be implemented in other ways than those described in this application, within the scope of the same inventive idea. Mathematical models, neural-network models, fuzzy-logic means, averaging, or some other parameters controlling the provision of feedback can be utilized when setting the limits. FIGS. 16a and 16b, which are described in greater detail later, show the boundary functions of the lower limit of the guidance area of the intensity, in certain cases.

Figure 5:
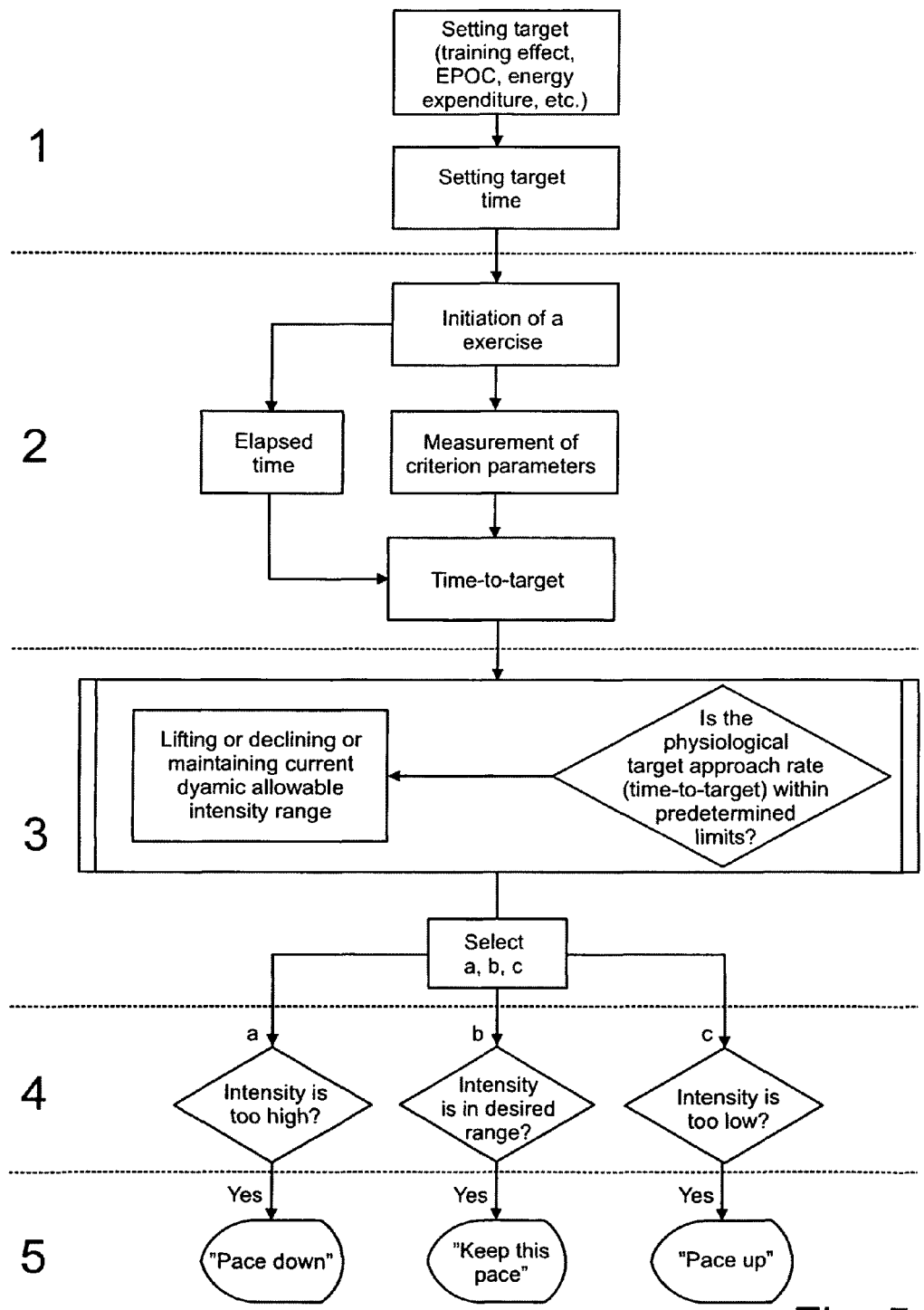
FIG. 5 shows a flow diagram for guiding exercise to a physiological target state within a target time.

FIG. 5 shows the basic principles for guiding exercise to a target state, including the following stages:
1. The user sets the physiological target state aimed at in the exercise, as well as the target time for reaching the set physiological target state.
2. The user starts the workout. During the workout, the time elapsed and the criterion variables (intensity of exercise) affecting the approaching of the physiological target state are measured, and with their aid the time, which will elapse at the prevailing intensity for reaching the set physiological target state, is determined.
3. Depending on the achievement of the physiological target state during the workout, the intensity range, by means of which the physiological target state can be reached in an acceptable time deviation relative to the target time, is adjusted during the workout. If the physiological target time is reached too rapidly or slowly at the start of the workout, the intensity requirement for the rest of the workout will increase or decrease correspondingly. The accepted intensity window can be from the greatest accepted intensity—that is dynamically adjusted—for example, by 30%-units downwards.
4. The estimate of the time taken to reach the target is compared with the predefined limits as to how much time it can take to reach the target at a specific moment in the workout. The limits are defined taking into account both physiological principles and those relating to user-friendliness. For example, the real duration of the workout can be either slightly longer or shorter than the target time, without the system being immediately to guide the performance differently. The progress of the workout can also be relatively free, as long as it proceeds towards the predefined target. Thus, it is determined when the intensity is suitable, too low, or too high.
   a. If the target state will be reached too late and the intensity deviates from the acceptable intensity range, the intensity must be increased.
   b. If the physiological target state will be reached too late, but the intensity is within the acceptable intensity range, the intensity is suitable.
   c. If the target state will be reached within the acceptable time limits, the intensity is suitable.
   d. If the target will be reached too early, the intensity must be reduced.
5. The user is given feedback at a given moment whether to keep the intensity the same, reduce the intensity, or increase the intensity. The feedback can be, for example, either visible or audible, or it can be implemented in other ways, for example, using various vibration alarms.

In one embodiment of the invention, EPOC (Excess post-exercise oxygen consumption)(e.g., Brooks, G. A. & Fahey, T. D., 1984, Exercise Physiology. Human bioenergetics and its applications. New York: Macmillan Publishing Company), or an training-effect value derived from it, can be used as the physiological target state. Nevertheless, it is obvious that the target can also be, for example, cumulative total energy consumption or net energy consumption, the amount of external work carried out, oxygen consumption, heart rate sum, mean heart rate, duration of exercise and mean intensity, Training Impulse (e.g., Banister, E. W., 1991, Modeling Elite Athletic Performance. In: MacDougall, J. D; Wenger, H. A.; & Green, H. J. (eds.), Physiological Testing of the High-Performance Athlete, $2^{nd}$. ed., Champaign, Ill.: Human Kinetics), or some physiological measure, which depicts exercise.

In one embodiment of the invention, the guidance criteria used are the elapsed time and the already accumulated EPOC or training effect level and the change in EPOC or training effect, as well as the predicted intensity (oxygen consumption relative to the person's maximum oxygen uptake), compared to the target. However, it is obvious that the guidance criteria used can also be momentary energy consumption, amount of energy consumed, momentary oxygen consumption, momentary oxygen consumption, accumulated oxygen consumption, distance, power of external work, or some other physiological measure, which depicts the exercise.

The target can be formed of several criteria, for example, a time-distance pair, in which case a natural guidance criterion would be speed. Other possible target pairs are, for example, time-energy consumption and energy consumption-training effect. For example, in the energy consumption-training effect pair, the guidance criterion is the rate of energy consumption (e.g., kcal/min), which produces a target time to which a specific training effect is applied. For example, the target can be a 900-kcal workout, in which a training effect of 3.0 is also achieved. This 3.0 training effect signifies an EPOC value of 62 ml/kg in the activity class 7. Intensity is thus attempted to be adjusted at each moment to be such that an energy amount of 900 kcal and a 62-ml/kg EPOC are reached at approximately the same time. At the start of workout, the rate of energy consumption could be, for example, 10 kcal/min, in which case the duration of the workout would be 90 minutes, so that the EPOC should accumulate at a rate of approximately 0.69 ml/kg/min. If the EPOC accumulation rate is so high that the training effect that is the target appears to be going to be reached well before the 900-kcal energy consumption is completed ('time to target' is too short), the user is advised to lower the intensity. If the 'time to target' is too long, but still within the expanded intensity range, the command will be to keep the intensity the same. In other cases, the command will be to increase the intensity. Of course, the intensity will be also ordered to be increased, if the EPOC drops faster than a predefined criterion (e.g., 1 ml/kg/min), or if one has drawn away from the predefined criterion (e.g., 1 ml/kg) earlier from the already achieved EPOC value farther than a predetermined criterion. The system thus returns through the calculation of the 'time to target' variable to the dynamic guidance described above with many examples.

In one embodiment of the invention, the intention is to remove impossible target pairs. Impossible target pairs can be removed, for example, when making the initial settings, or even when the exercise targets are altered after the workout has already been started.

Figure 6A:
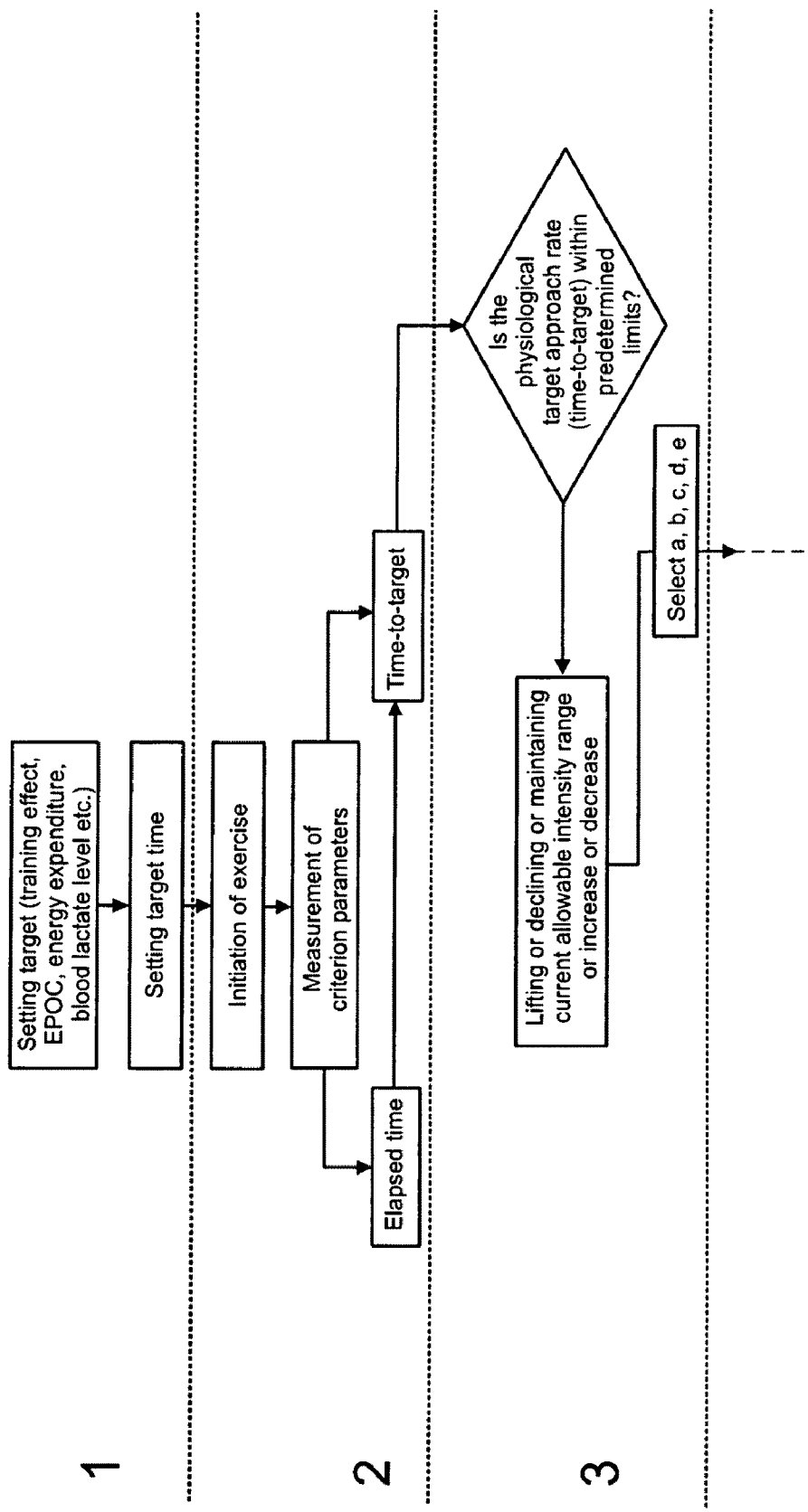
FIG. 6 shows one detailed embodiment for guiding exercise to a physiological target state within a target time.
Figure 6B:
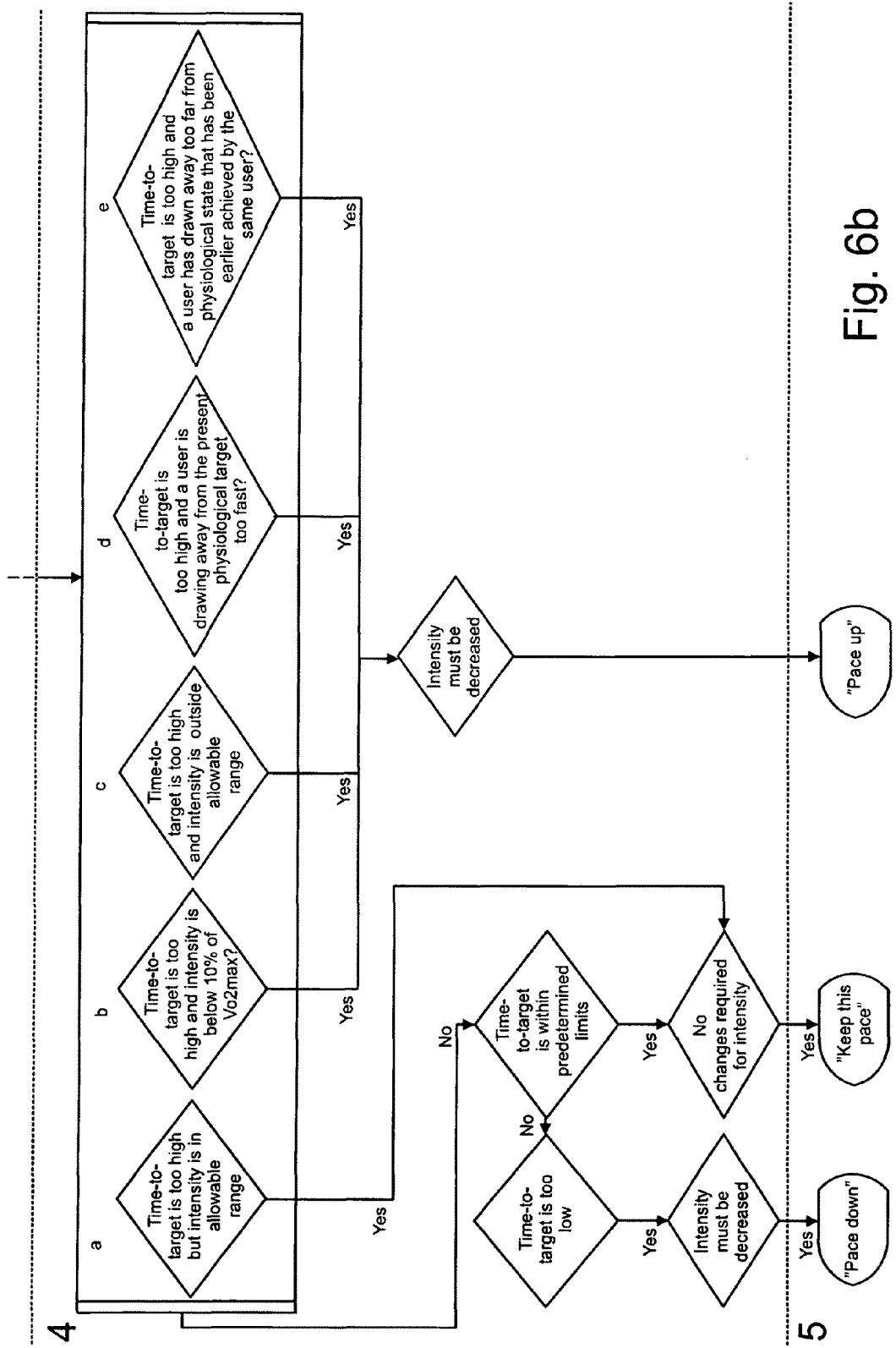

One possible embodiment of the invention, shown in FIGS. 6a and 6b, contains the following stages for guiding exercise to a physiological target state:
1. The user sets the physiological target state, at which the exercise is aimed, and a target time for reaching the set physiological target state.
2. The user starts the workout. During the workout, the time elapsed and the criterion variables (exercise intensity) affecting the reaching of the physiological target state are measured, with the aid of which the time required to reach the set physiological target state can be determined.
3. Depending on reaching the physiological target state in the course of the workout, the greatest accepted intensity, by means of which the physiological target state will still be achieved within the acceptable limit before the set target time, is predicted and dynamically adjusted in the course of the workout. If the physiological target state is reached at the start of the workout more rapidly or slowly, the intensity requirement for the remainder of the workout correspondingly decreases or increases. The accepted intensity window is, for example, 30%-units down from the greatest accepted dynamically changing intensity (e.g., % VO2max).
4. The estimated time taken to reach the target is compared with the predefined limits, which determine how long a time it is accepted to elapse before reaching the target at a given moment of the workout. The limits are defined taking into account principles relating to both physiology and user-friendliness. For example, the predicted duration of the workout can be either slightly shorter or longer than the target time, without the system beginning immediately to guide the exercise differently. The progress of the workout can also be relatively free, as long as it progresses towards the predefined target. Thus it is defined when the intensity is suitable, too low, or too high (FIG. 6b, Section 4).
   a. If the target will be reached too late and the intensity is too low, the intensity must be increased.
   b. If the target will be reached too late and one is drawing away from the physiological target state faster than a predefined criterion, the intensity must be increased.
   c. If the physiological target state will be reached too late and one has already drawn away from an already reached physiological state farther than the predefined criterion, the intensity must be increased.
   d. If the physiological target state will be reached too late and the intensity deviates from the accepted intensity range, the intensity must be increased.
   e. If the target will be reached within the accepted time limits, the intensity is suitable.
   f. If the physiological target state will be reached too late, but the intensity is in the accepted intensity range, and one is not drawing away too quickly or far from the physiological target state, the intensity is suitable.
   g. If the target will be reached too early, the intensity must be reduced.
5. At a specific moment, the user is provided with feedback to keep the intensity the same, to reduce the intensity, or to increase the intensity. The feedback can be, for example, either visual or auditive, or it can be implemented by other means, for example, using various vibration alarms.

Different kinds of guidance criteria can also be used for the same target (e.g., the rate of change of energy consumption as the guidance criterion for training effect, the rate of change of EPOC and/or the accumulation for the training effect), in which case the target can, for example, be stabilized and the guidance criterion altered. Naturally, the variables can also be altered to act in the opposite direction. The guidance criterion can also be dynamic, in which case different criteria will be used at different stages of the workout, which may be possible, for example, in interval training. Some targets are bound to specific target criteria (and vice versa).

Figure 7A:
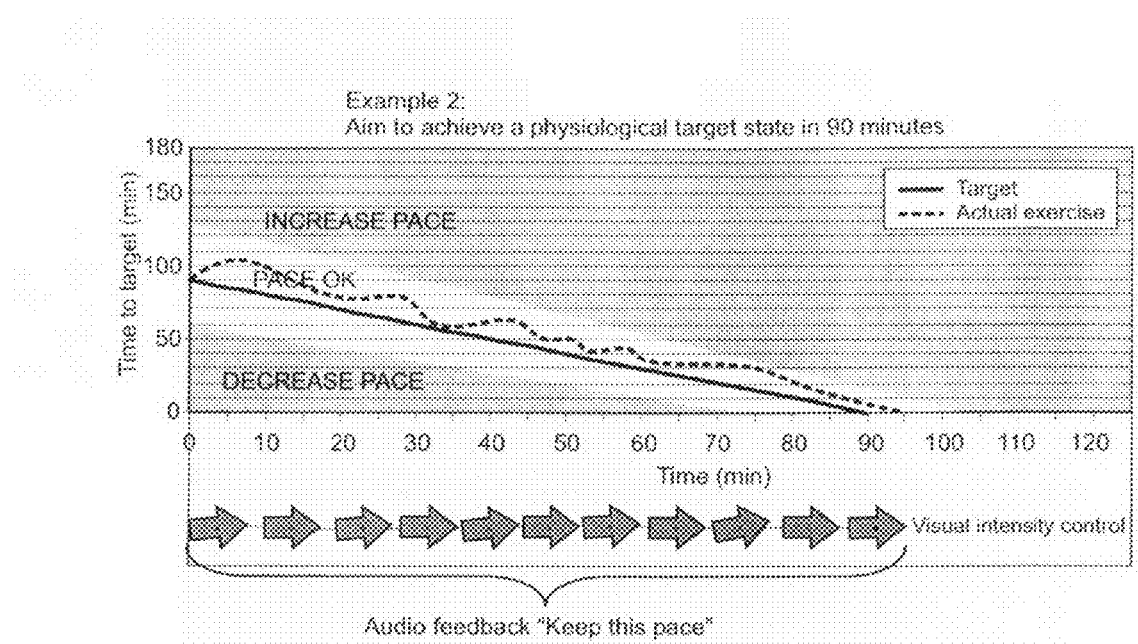
FIGS. 7a, 7b, and 7c, as well as 8a, 8b, and 8c show two different exercises guided to a physiological target state and examples of the visual and auditive feedback given to the user.
Figure 7B:
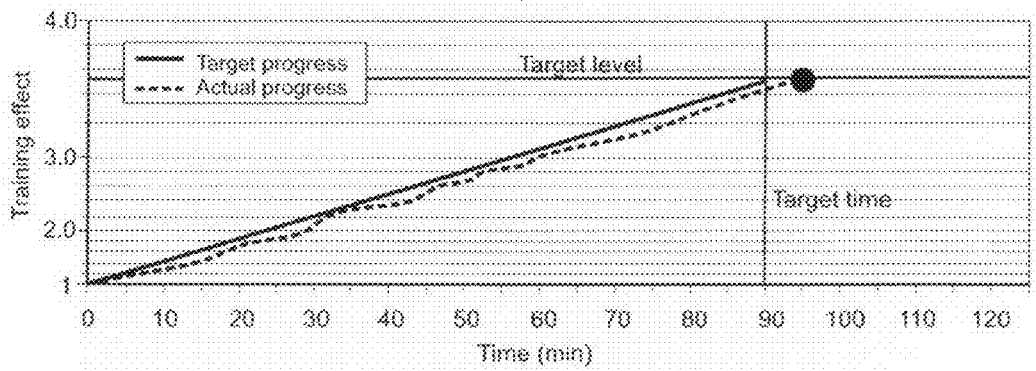
Figure 7C:
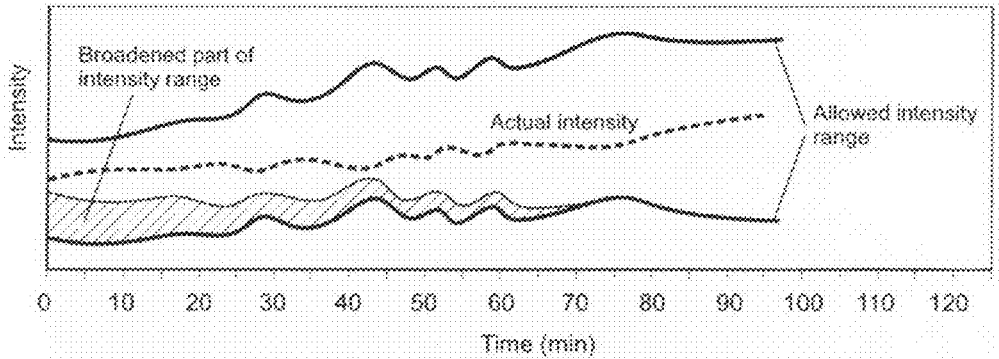

Example 2 (FIGS. 7a-7c) shows a workout, in which the target is to reach a specific physiological state during a period of 90 minutes, which physiological target state is, in this example, exercise developing a training effect of 3.5, on a scale 1.0-5.0. Feedback is naturally given to the user in real time during the workout. The system permits a deviation in the duration of the workout of about fifteen minutes from the target time, both longer and shorter, to increase user friendliness. Even though the intensity (FIG. 7c) varies during workout, the 'time to target' (FIG. 7c) nevertheless remains all the time within the range from which the system gives the 'suitable speed' feedback (FIG. 7a), and the target of the workout is finally reached after 95 minutes (FIG. 7b).

Figure 8A:
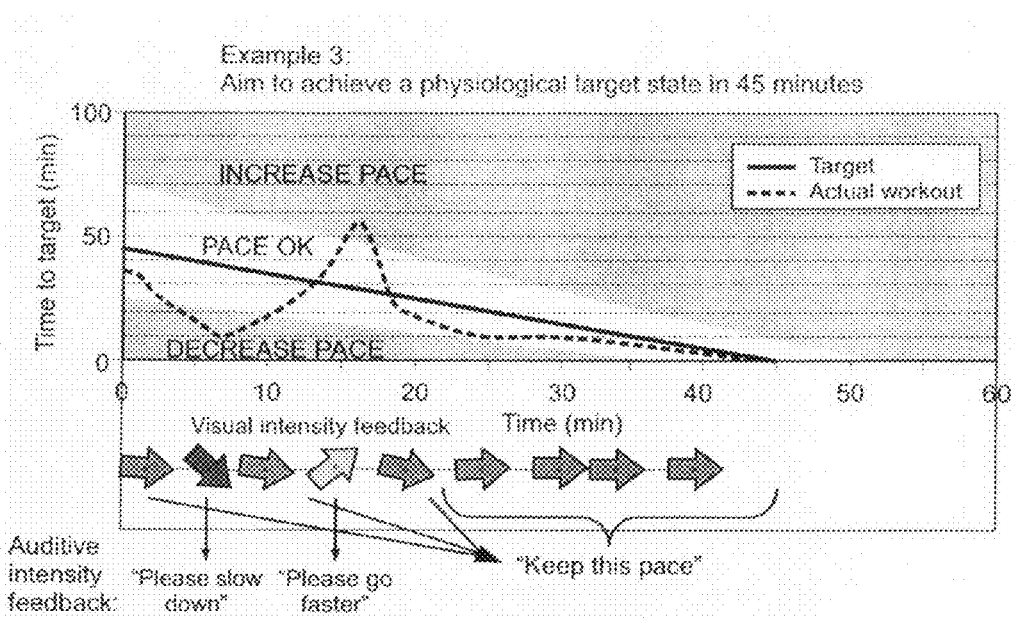
Figure 8B:
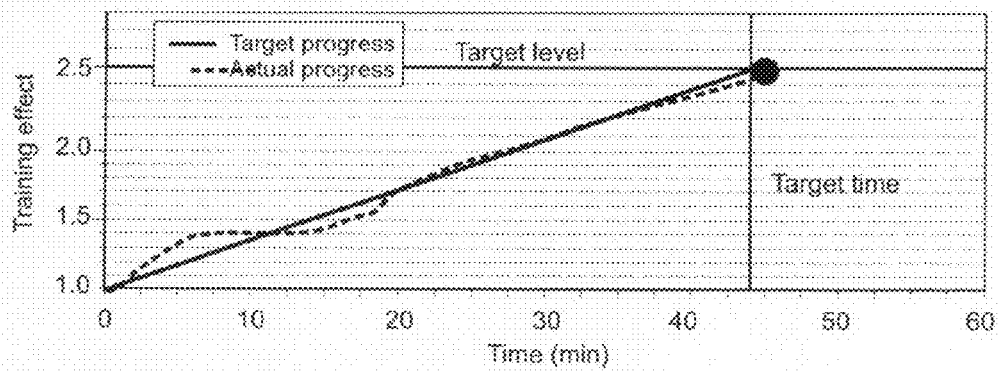
Figure 8C:
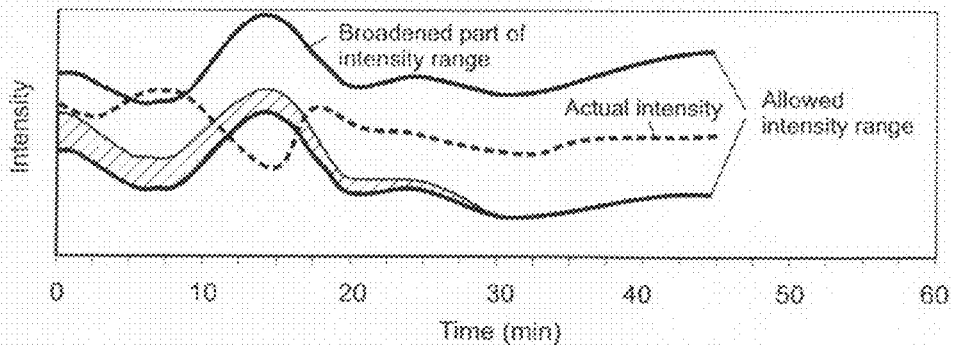

Example 3 (FIGS. 8a-8c) shows workout, in which the user of the device has defined the target time of the workout as 44 minutes and the training-effect target as a training effect that maintains a value of 2.5. At the start, the user moves with slightly too high an intensity (FIG. 8c) relative to the feedback (FIG. 8s), thus reaching the target (FIG. 8b) too soon, in which case the system commands the user to decrease the intensity. As the user reduces the intensity to a suitable level on the basis of the feedback, the target will now be reached in the target time. If, despite everything, the user moves after this at too low intensity, the system gives a command to increase the intensity. Having followed the instructions given by the intensity guidance in the final part of the workout, the user reaches the set target in more or less the target time (FIG. 8b).

In Example 3, the permitted intensity range changes dynamically as the workout proceeds, depending on the progress of the workout. As the user moved at slightly too high an intensity at the start of the workout, the intensity requirement dropped, and correspondingly when the user moved at too low an intensity the intensity requirement increased.

It can be seen from the example graphs that, as the target time approaches, it is no longer possible to obtain feedback for a more extreme increase in intensity. This is not a drawback, because from a physiological point of view it is not so important to reach the target in exactly the set time. In practice, this means that at the end the user can exercise as hard as possible, but will not be given maximum slowing feedback. However, in this case the user receives less compelling feedback to reduce speed.

Once the set target time has been reached, the user can be given an 'exercise-time exceeded' message. After this, arrow feedback is still provided according to the zones in FIGS. 7 and 8. From now on, according to the graphs, s feedback to slightly increase intensity will become impossible to achieve and if the max limit is exceeded, after this there will be no alternative except to give maximum feedback to increase intensity.

Once the set physiological target is reached, the user can be informed that 'target reached' and the display of intensity guidance can be terminated.

Figure 9:
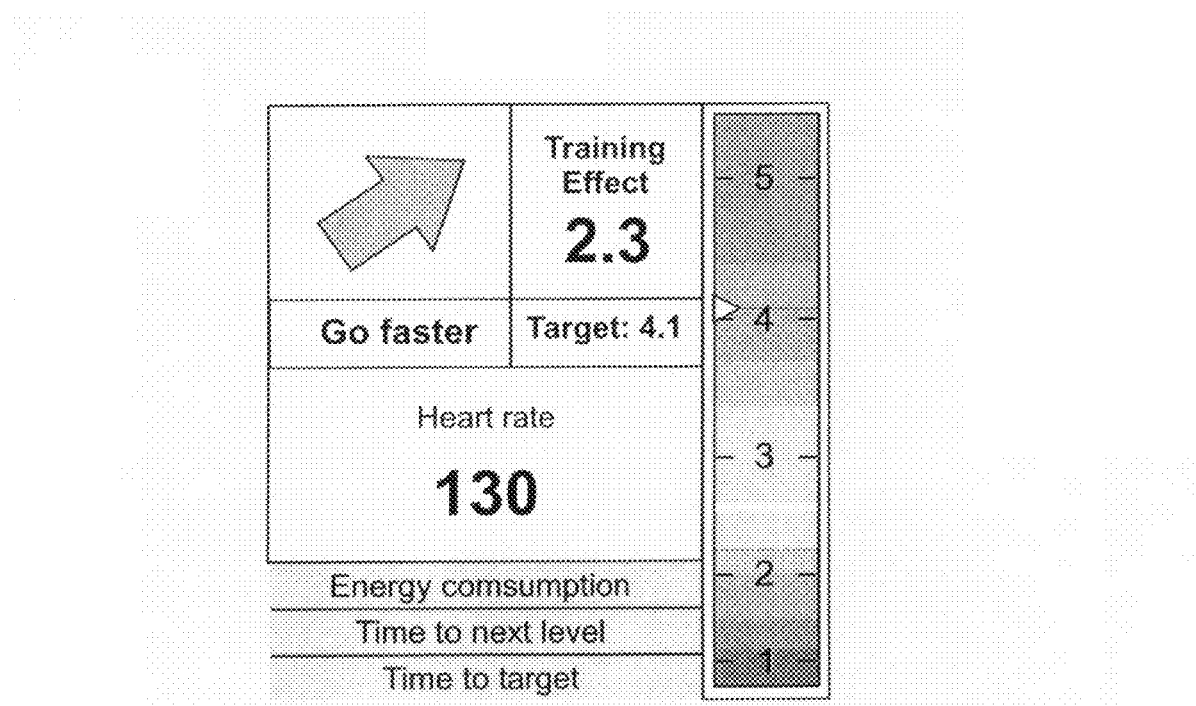
FIG. 9 shows one embodiment of a mobile user interface of a dynamic guidance system.

FIG. 9 shows an example of a mobile user interface. In one embodiment of the invention, the display of a mobile terminal is used to show information on the already achieved training effect, the exercise target, and the heart rate, as well as to give visual feedback (arrow and text 'go faster'), which can be reinforced with auditive feedback, or using, for example, various vibration alarms. Though the interface it is also possible to browse energy consumption, the time estimated to elapse before reaching the next training-effect level (time to next level), as well as the time estimated to elapse before reaching the target (time to target). In one embodiment, at least two forms of feedback are used, of which one, generally visual, is detached from the expansion, i.e. displays the guidance without expansion (not shown).

Figure 10:
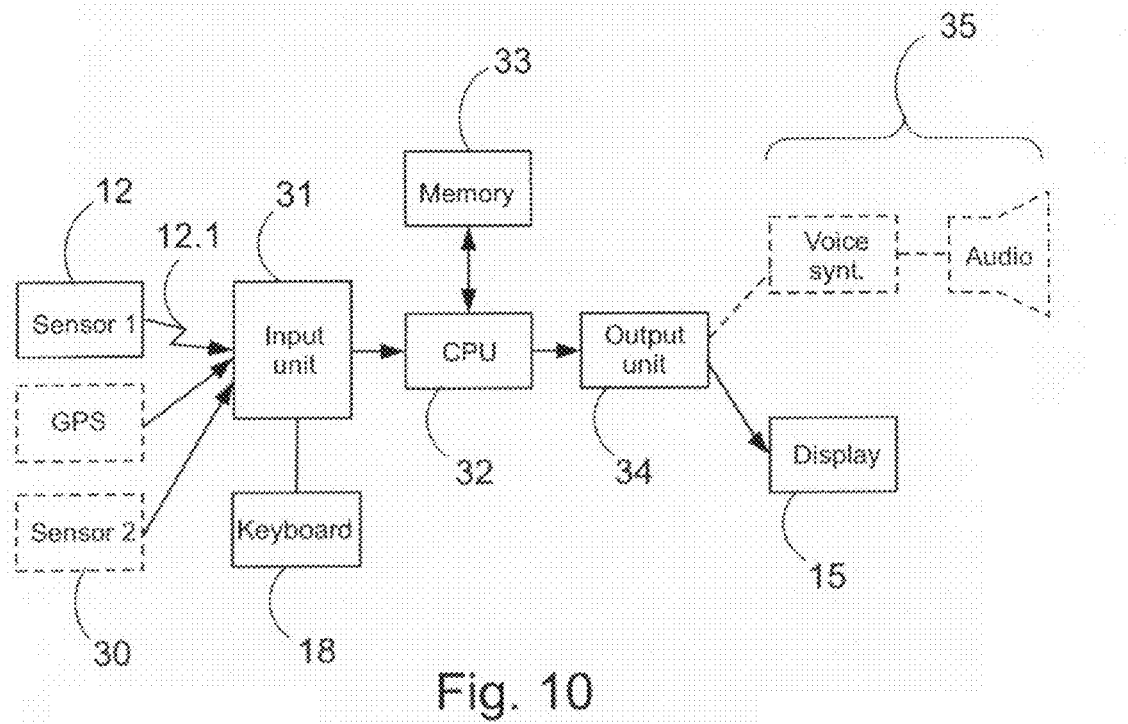
FIG. 10 shows a schematic diagram of an apparatus, by means of which the disclosed invention can be implemented.

FIG. 10 shows, in addition, one embodiment of the apparatus required by the invention, containing the necessary means for recording values, means for giving feedback, means for positioning the person and recording and processing route data, and program means, including measuring sensors 12, 30, a keypad 18 and unit 31 for entering information, a central unit 32, a memory 33, an output unit 34, a display 15, and possibly a voice synthesizer and loudspeakers 35. Typically the device involved is a PC; a PDA device, or a wristop computer. Other sensors (such as a GPS positioning unit and/or barometer) will be required, especially in connection with the distance/route application described later.

In one embodiment of the invention, the control logic can be used to produce visual intensity guidance, with the aid of a yellow-green-red arrow, through simple text feedback, and as voice feedback. For guidance, the basic variables should be set, i.e. the target time, the target, and the guidance criteria. The guidance is calculated on the basis of specific permitted deviations to the 'time to target', relative to the remaining exercise time. In the guidance, the same time 'time to target' is used as that displayed to the user, i.e. it can also have a limited increase (compare Example 4 on Page 20). This will permit unified feedback.

Minute-level precision is not required in reaching the exercise time target, but only sensible limits, which are not yet of great significance in terms of the effect of the exercise. I.e. the permit limits are ±6 min. for a 30-min. exercise target, ±8 min. for 45-min. exercise, ±10 min. for 60 min., ±15 min. for 120 min., and ±20 for 180 min. Generally, the tolerance is at most 10 minutes+15% of the nominal value of the duration.

Both the 'time to target' and the position of the guidance arrow are calculated using limited 'time to target' information, i.e. the limitation also appears in the operation of the guidance arrow.

In one embodiment of the invention, some degree of intensity variation is permitted, but despite this the exercise is guided to a time target. The intensity range, which is still in the 'intensity ok' range (FIGS. 2 and 3) is 30% VO2max down from the intensity calculated from the $T_{ok-}$ limit (FIGS. 2 and 3), i.e. 30%-units down from the greatest permitted % VO2mas value, at which 'keep this pace' is still displayed. I.e. if this greatest intensity is, for instance, (at TE target 3.0 and exercise time 30 min.) 70% VO2max, then when moving in the area 40-70% VO2max the feedback will be 'pace ok'. However, if at the same time the EPOC also drops faster than the selected criterion, the feedback will then be 'go faster'. Thus a slow drop will also be permitted in EPOC during exercise, without the user being commanded to increase the intensity. In addition, in EPOC, however, a small drop (1 ml/kg) will be permitted, compared to the highest value of the exercise up to that point, before the feedback 'go faster' is returned, which will smoothen the feedback to be more comfortable. However, if the EPOC has dropped more than the pre-selected criterion—for example, 1 ml/kg—compared to the higher value of the exercise up to that point, the user will be commanded to increase the intensity. This feedback will be given, even if the user was within the permitted 30%-unit-wide intensity range. The intensity range can, of course, be any other corresponding predefined intensity range.

One embodiment is to use the aforementioned control logic combined with voice guidance. In addition, all the other real-time information on the progress of the workout can be converted to voice information, for example, when the user selects specific feedback and its form.

TABLE 1

Correspondences between visible and audible feedback

| Feedback group (Difference to desired time-to-target value | Content of text and audible feedback | Direction of arrow (visual feedback) | Colour of arrow |
|---|---|---|---|
| 1- 'Faster'- imperative feedback (very large difference) | Faster<br>Faster<br>Faster | 45° upward<br>39° upward<br>33° upward | Yellow<br>Yellow<br>Yellow |
| 2. 'Faster' - neutral feedback (large difference) | Faster<br>Faster<br>Faster | 27° upward<br>22° upward<br>16° upward | Yellow<br>Yellow<br>Yellow |
| 3. 'Pace OK' - encouragement or neutral feedback (no difference or small difference) | Pace ok<br>Pace ok<br>Pace ok<br>Pace ok<br>Pace ok | 11° upward<br>5° upward<br>0°<br>5° downward<br>11° downward | Green<br>Green<br>Green<br>Green<br>Green |
| 4. 'Slower' - neutral feedback (large | Slower<br>Slower | 16° downward<br>22° downward | Red<br>Red |

TABLE 1-continued

Correspondences between visible and audible feedback

| Feedback group (Difference to desired time-to-target value) | Content of text and audible feedback | Direction of arrow (visual feedback) | Colour of arrow |
|---|---|---|---|
| difference | Slower | 27° downward | Red |
| 5. 'Slower'- | Slower | 33° downward | Red |
| imperative feedback | Slower | 39° downward | Red |
| (very large difference) | Slower | 45° downward | Red |

In one embodiment of the invention, the guidance linked to the control logic can be given based on numerical or graphical information on the progress of the workout, given on the display (for example, based on the EPOC accumulation, or on the 'time to target' numerical information on the display). Table 1 shows the correspondences of the visual and auditive feedback of the guidance. The greater the difference between the 'time to target' value at the time and the present target range (expert-time limits 'keep this pace' range, FIGS. 2 and 3), the more commanding is the auditive feedback and the stronger is the visual feedback, which in this embodiment is depicted by the steepness of the guidance arrow and the changing colour of the arrow.

In order to achieve a pleasant result from the user's point of view, the voice feedback should be modified. By default, voice feedback of the corresponding feedback group according to Table 1 is given, if the exercise has remained on a level corresponding to the feedback group for 15 seconds. After that, if it remains on the same level, voice feedback will continue to be given at 2-minute intervals. I.e. if a change to another group and back takes place in less than 15 seconds, no voice feedback will be given. In addition, the voice feedback can be modified in such a way that, if the user should move faster or slower, but still remains at this level for example for 4 minutes, voice feedback will be given more frequently, or a more serious feedback command to change intensity will be returned, in order to make the user reach the target. In addition, if the intensity remains at a suitable level for a longer period, voice feedback can be given less frequently, or even omitted entirely, thus notifying the user that the intensity is suitable, if no feedback is received. Naturally, different default alternatives for the frequency of the voice feedback can be set for selection from the user interface, for example 'frequent' (time limits shorter), 'normal', or 'seldom' (time limits longer).

In one embodiment of the invention, the time prediction for reaching the target can be limited, in order to improve the usability and understandability of the predictions. By default, neither the 'time to target' nor the 'time to next level' time predictions are accepted to increase by more than 10 minutes a time at 5-second intervals. The value can be adjusted from the user interface, for example, to values of 0, 1, 3, 5, 10, 15, 20, and 30 minutes. At the value zero, the time prediction is not limited. A stepped increase in the time prediction by the amount of the set maximum value is also performed if the time prediction in question begins to show 'out of reach' (displayed to the user, if the 'time to target' or 'time to next level' is more than 180 minutes). In other words, the time prediction is calculated internally to 190, 200, etc., but this not displayed to the user. In the embodiment in question, the decrease in the time prediction would not be limited.

Example 4: 'time to target' shows 10 min. The user is skiing and descending a hill, during which time the intensity decreases, the prediction showing 30 minutes after a 5-second descent and 'out of reach' after a 45-second descent. In this case, starting from the top of the rise, the prediction is increased as follows at 5-second intervals: 10, 20, 30, 40, 50, 60, 70, 80, 90, 100 minutes. If the user starts skiing again after the descent, and the intensity increases, the prediction is not limited and indeed soon shows again 10 minutes to target. If the increase in the time prediction were not to be limited, the target would usually escape to the 'out of reach' state, irrespective of the length of the descent (duration of recovery).

In one embodiment of the invention, the user sets either specific training effect, or an EPOC value and target time as the target. The specific training-effect level always corresponds to a specific EPOC value. If the user has selected a specific training-effect target, it is converted in the system to a corresponding EPOC target, which can, if desired, show in addition the selected training-effect target to the user. In this case, the guidance contains the following stages:

1. The user sets the target EPOC value, or the target training effect, at which the workout is aimed, as well as the target time for reaching the target state.
2. The user starts the workout. During the workout, the time elapsed and the intensity (% VO2max or the EPOC's accumulation rate ml/kg/min), with the aid of which the time that will elapse to reach the EPOC/training effect set as the target is determined.
3. Depending on the achievement of the EPOC/training-effect target during the progress of the workout, the greatest intensity, at which the EPOC/training-effect target will still be reached within the accepted limit before the set target time, is adjusted during the workout. The accepted intensity range is, for example, 30%-units down from this dynamically adjusted greatest intensity (e.g., % VO2max). If the EPOC/training-effect target is reached too quickly, or slowly at the beginning of the exercise, the required intensity range for the remainder of the workout correspondingly decreases or increases.
4. The time estimated as elapsing before the EPOC/training-effect target is compared to the predefined limits, which determine how long a time may elapse before reaching the target at a given moment in the workout. The limits are defined taking into account principles relating to both physiology and user friendliness. For example, the real duration of the workout can be either slightly shorter or longer than the target time, without the system immediately beginning to guide the workout differently. The progress of the workout can also be relatively free, as long as it proceeds towards the predefined target. It is thus determined when the intensity is suitable, too low, or too high.
   a. If the target will be reached too late and the intensity is too low, the intensity must be increased.
   b. If the EPOC/training-effect target will be reached too late and the EPOC will decrease too rapidly, the intensity must be increased.
   c. If the EPOC/training-effect target will be reached too late and one has already drawn away too far from the EPOC value already achieved, the intensity must be increased.
   d. If the EPOC/training-effect target will be reached too late and the intensity deviates from the accepted intensity range, the intensity must be increased.
   e. If the EPOC/training-effect target will be reached within the accepted time limits, the intensity is suitable.
   f. If the EPOC/training-effect target will be reached too late, but the intensity is within the accepted intensity range, and one is not drawing away too rapidly or far from the EPOC value already reached, the intensity is suitable.

g. If the EPOC/training-effect target will be reached too early, the intensity must be reduced.

5. The user is given feedback at a given moment as to whether to keep the intensity the same, reduce the intensity, or increase the intensity. The feedback can be, for example, either visible or audible, or it can be implemented by other means, for example, using various vibration alarms.

In one embodiment of the invention, the target is a given cumulative energy consumption, weight reduction, fat consumption, carbohydrate consumption, or some other variable that can be calculated. The user is guided to the target state within a predefined target time. The guidance consists of the following stages:

1. The user sets the physiological target energy consumption, target weight reduction, target fat consumption, target carbohydrate consumption, or some other corresponding variable that can be calculated, at which the workout is aimed, as well as the target time for reaching the set target.

2. The user starts the workout. During the workout, the time elapsed is measured, as well as the criterion variables affecting the achievement of the target (consumed energy and present energy consumption/time unit, reduced weight and rate of weight reduction/time unit, consumed fat and amount of fat consumed/time unit, consumed carbohydrates and consumption of carbohydrates/time unit), with the aid of which it is possible to determine the time that will elapse for reaching the set target at the present rate of consumption of energy, fat, or carbohydrates, or the rate of weight reduction.

3. Depending on the rate of consumption or weight reduction during the workout, the target consumption range, by which the target state will be reached within an accepted time deviation relative to the target time, is predicted and dynamically adjusted during the workout. If the target state will be reached too quickly or slowly at the start of the workout, the consumption requirement or weight-reduction requirement for the remainder of the workout will be correspondingly decreased or increased. The target range of the rate of consumption of energy, fat, or carbohydrates, or the rate of weight reduction is defined to be such as will permit comfortable feedback.

4. The estimated time for reaching the target is compared with the predefined limits, which determined how long it can take to reach the target, at a given moment during the workout. The limits are defined taking into account the principles of both physiology and user-friendliness. For example, the real duration of the workout can be either slightly shorter or longer than the target time, without the system beginning immediately to guide the application differently. The progress of the workout can also be relatively free, as long as it proceeds towards the predefined target. Thus, it is determined when the intensity is suitable, too low, or too high.

a. If the target state will be reached too late and the intensity deviates from the accepted rate of consumption of energy, fat, or carbohydrates, or rate of reduction of weight, the intensity must be increased.

b. If the target state will be reached too late, but the rate of consumption of energy, fat, or carbohydrates, or the rate of weight reduction is within the accepted intensity range, the intensity is suitable.

c. If the target state will be reached within the accepted time limits, the intensity is suitable.

d. If the target will be reached too early, the intensity must be reduced.

5. The user is given feedback at a given moment as to whether the rate of consumption of energy, fat, or carbohydrates, or the rate of reduction of weight should be kept the same, or decreased, or decreased. The feedback can be, for example, either visual or auditive, or it can be implemented by other means, for example, using various vibration alarms.

In one embodiment of the invention, the target can be to perform a specific distance within a target time. The guidance to the target then consists of the following stages:

1. The user sets the physiological target distance, which is aimed at in the workout, as well as the target time for achieving the set target distance.

2. The user starts the workout. During the workout, the time elapsed is measured, as are the criterion variables (speed of exercise) affecting the achievement of the target distance, with the aid of which the time, which will elapse at the present speed to reach the set target distance, is determined.

3. Depending on the accumulation of distance during the workout, the speed range, by which the target distance will be achieved within the accepted time deviation relative to the target time, is predicted and dynamically adjusted during the workout. If the distance is being covered too quickly or slowly at the start of the workout, the speed requirement for the remainder of the workout is correspondingly decreased or increased. The accepted speed range is determined based on the dynamically changing highest speed, and is, for example, in cycling 5 km/h lower value than highest speed and in running 2 km/h lower value than highest speed.

4. The estimated time taken to achieve the distance target is compared to the predefined limits, which determine how much time can elapse to achieve the target at a given moment during the workout. The limits are defined taking into account the principles relating to both physiology and user-friendliness, for example, in such a way that a running speed that is too high and impossible for the user can not be left to the remaining part of the workout. Impossible situations are excluded on the basis of the fitness level of the user, of which an example is shown in FIG. 16a, a detailed description of which figure is given later. The real duration of the workout can also be slightly shorter or longer than the target time, without the system being immediately to guide the workout differently. The progress of the workout can also be relatively free, as long as it proceeds towards the predefined distance target. Thus it is determined when the speed is suitable, too low, or too high.

a. If the target distance will be achieved too late, and the speed deviates from the accepted speed range, the speed must be increased.

b. If the target distance will be achieved too late, but the speed is within the accepted speed range, the speed is suitable.

c. If the target distance will be achieved within the accepted time limits, the speed is suitable.

d. If the target distance will be achieved too early, the speed must be reduced.

5. At a given moment, the user is given feedback as to whether to keep the speed the same, decrease the speed, or increase the speed. The feedback can be, for example, either visual or auditive.

In one embodiment of the invention, the target of the workout can be altered after the workout is already under way. The target of the workout could be altered, for example, relative to energy consumption, from 500 kcal to 600 kcal, or the training effect from 3.0 to 3.5, in the middle of the workout. In the same way, the target time, target distance/target route could be altered.

In one embodiment of the invention, the target state is a specific amount of physiological recovery or relaxation, which must be achieved within a specific time, for example, from the end of the present workday to the start of the following workday. With the aid of this, it is possible to guide a person to actively recover, or to make choices that will help them to recover.

In one embodiment of the invention, the target state is a specific amount of stress, which must be reached within a specific time, for example, during a workday.

One or more variables, measured either directly or on the basis of heart rate (speed), or physiological variables (heart rate, oxygen consumption, respiration rate, ventilation) can be used to measure intensity. The change in EPOC can be calculated as the difference between present and previous EPOC. Ml/kg/min can be used as the unit and the result converted to it. The change in energy consumption (kcal/min) and the change in distance (km/min) can also be calculated.

In one embodiment of the invention, the user sets a physiological target state and a target time. The speed and altitude of the user are measured (angle of ascent/descent) with the aid of GPS positioning and possibly air-pressure measurement, or by combining acceleration measurement and air-pressure measurement. The maximum oxygen uptake (VO2max) of the user is known. It is either given by the user, calculated on the basis of the physiological background data given by the user, or a default value is used. The intensity is calculated on the basis of the speed and altitude information, as well as of the user's maximum oxygen-intake ability. In the embodiment in question, the estimate of the 'time to physiological target' is compared with the target time, and current intensity is compared with the accepted intensity range, and the user is given intensity guidance, as described in the previous examples.

In one embodiment of the invention, the user can select preset types of exercise (see Table 2), in which the intensity of the user is guided and which types are generally known by name and effect. The exercise can be, for example, fat-burning exercise, basic endurance exercise, fast distance exercise maximum oxygen uptake (VO2max) exercise, recovery exercise, weight-management exercise, or some other similar exercise, in which the user is guided during exercise as described previously in this document. In the user-interface, the user is only presented with the name of the exercise (defined in Table 2, the name also includes the duration of the workouts, given in brackets), by selecting which the system moves to real time display and the workout is started. If desired, the user then sees what the real physiological target state is and the duration of the workout.

TABLE 2

Example exercise stated relative to training effect
(= physiological target state) and target time.

| Name of exercise | Warm up (training-effect target (1.0-5.0)/ target time) | Exercise portion (training-effect target (1.0-5.0)/ target time) | Duration of cool down (min.) |
|---|---|---|---|
| Fitness workout, hard (40 min.) | 1.5/5 min. | 3.5/30 min. | 5 |
| Fitness workout, medium (30 min.) | — | 2.5/30 min. | — |
| Fitness workout, easy (30 min.) | — | 2.0/30 min. | — |
| Burn calories (60 min.) | 1.5/5 min. | 3.8/50 min. | 5 |
| Burn fat (90 min.) | — | 2.5/90 min. | — |
| Recovery workout (30 min.) | — | 1.5/30 min. | — |
| Basic endurance short (60 min.) | — | 2.0/60 min. | — |
| Basic endurance long (90 min.) | — | 2.0/90 min. | — |
| *Fast distance training (55 min.) | 1.5/5 min. | 3.2/45 min. | 5 |
| *VO2max workout (45 min.) | 1.5/10 min. | 4.0/25 min. | 10 |

As an exception to the exercise intensity guidance described above, warming up forms part of the total exercise time, but does not shorten the actual target time of the exercise (shown in the table). The actual target can be different in warming up, the workout itself, and cooling down. At the start of the workout, the user is notified by both text and voice feedback that 'warm-up period in progress'. In one embodiment of the invention, the text appears on the display for 15 seconds from the start of the workout.

In one embodiment of the invention, warming up is guided to its target according to the TE and time target shown in the table. If the user reaches the TE value set as the target of the warm up earlier than the set time target, warming up is terminated and the actual workout is started. If the user does not reach the TE target within the time target set for the warm up, they can either continue the warm up to the end, or start the actual workout if they want to.

In one embodiment of the invention, the user is informed that warm up has ended, by both text and voice feedback, for example, that 'warm-up completed, workout starting'. The text is shown on the display for 15 seconds. The workout continues normally from the level that has been achieved (EPOC is not reset to zero), instead only a new TE and time target are set (shown in the table). In other words, if the length of the warm up is 5 minutes, and the duration of the actual workout is 30 minutes, according to the running time, the target will be reached at 35 minutes. The workout proceeds from this as a normal workout, the TE and time targets of which are set manually. Once the workout has ended, the user is notified normally of the achievement of the target, and after this is notified by both text and voice feedback, for example, that 'workout completed, start to cool down'. The workout does not end once the workout time has elapsed, but instead when the TE target has been reached. If the workout time is exceeded, the operations are the same as in the case of normal manually set targets.

In one embodiment of the invention, cooling down is guided on the basis of intensity, in such a way that 'pace ok' or 'suitable intensity' is shown (pace-arrow in the table above, which indicates completely ok speed), once the intensity is 30-50% VO2max.

Figure 11:
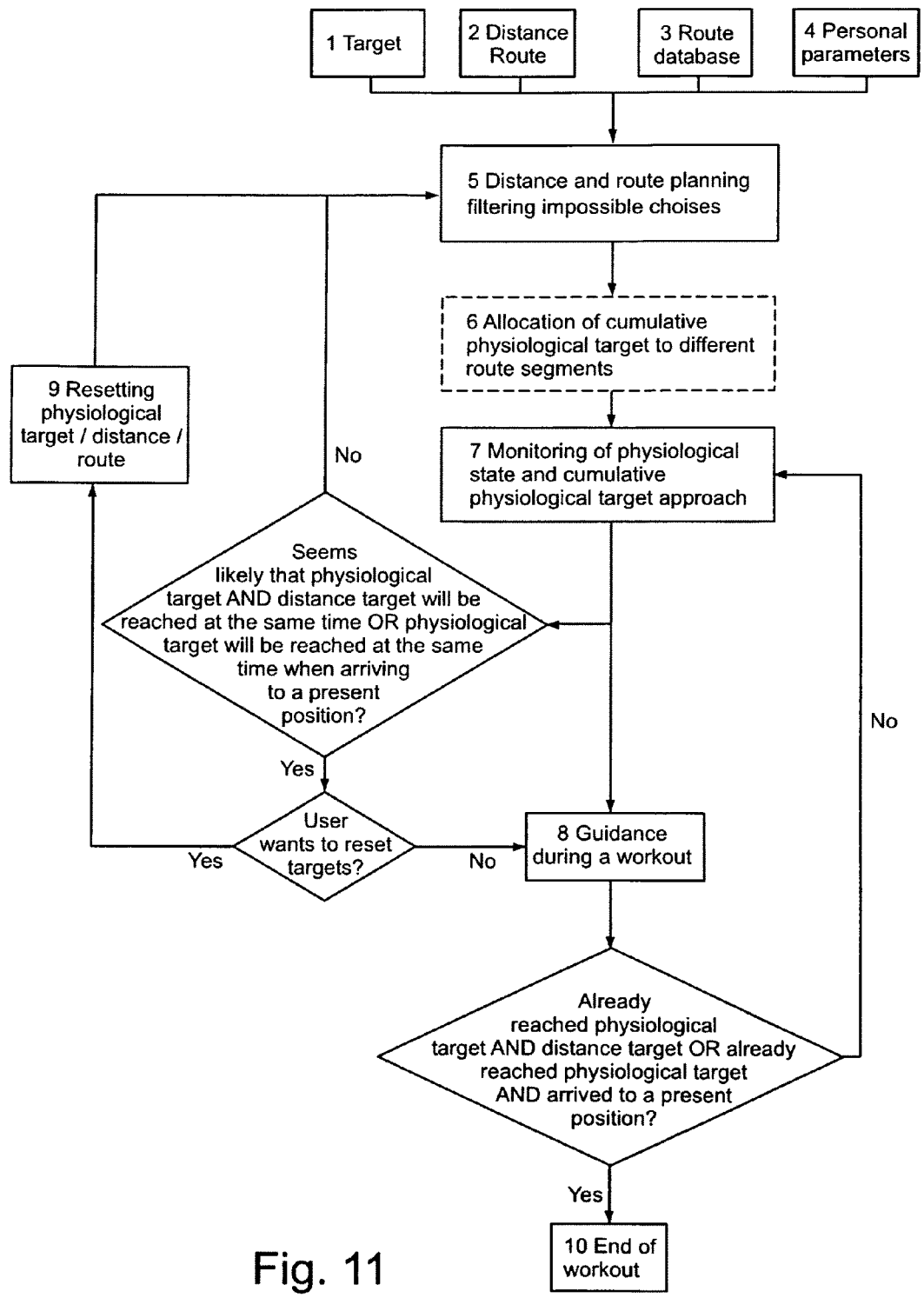
FIG. 11 shows a general flow diagram for guiding distance/route-based exercise to a physiologic al target.

FIG. 11 shows a flow diagram of how a distance and route-based guidance system, guiding exercise to a specific physiological target state, functions.

Figure 12:
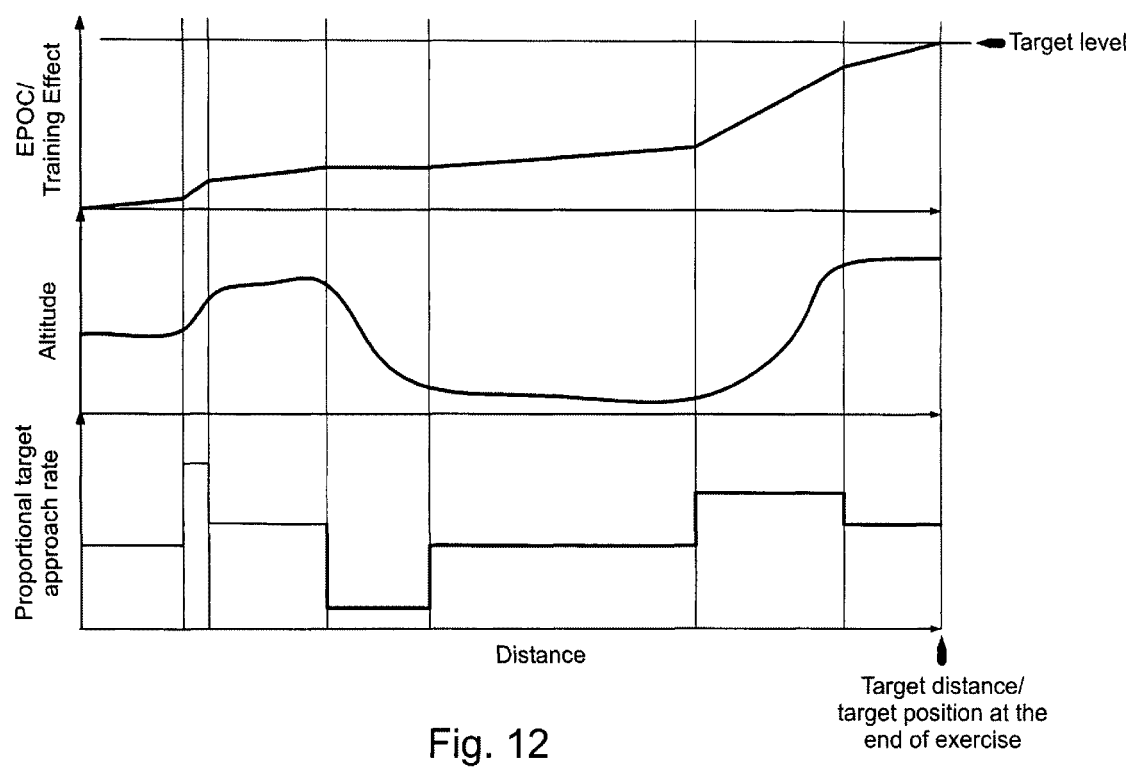
FIG. 12 shows how the system according to one embodiment allocates the achievement of a physiological target and distance target intelligently during exercise, on the basis of altitude data.

Explanations for the numbers of FIG. 11:
1. Setting the target of the exercise (EPOC (excess post-exercise oxygen consumption), training effect, energy consumption, heart-rate sum, TRIMP (training impulse), work amount (J), power output of work, mean heart rate, mean intensity, or some other quantity that essentially depicts the exercise).
2. Setting a specific distance or route as the target. Route information includes, altitude information for different stages of the route. The distance/route can be either selected from previous performances, or selected from, for example, a route database (Section 3).
3. The route database contains, for example, ready-to-use routes, a complete set of maps (roads, paths, streets, etc.), and well as the corresponding altitude data.
4. The background data of the person can contain, for example, the person's age, height, weight, sex, activity class, maximum heart rate, maximum oxygen consumption (VO2max), or some other variable, which depicts the level of person's performance ability, or other data that depict the person.
5. The distance/route is planned in such a way that a pleasant experience is created for the user.
   It is also checked if it is possible to reach the target with the framework of the distance/route within sensible limits. If it cannot be reached, the target or distance/route must be readjusted. For example, on the basis of the person's background data (fitness level) it is possible to estimate what speed the person can actually move in various forms of work, as well as to evaluate what kind of physiological response (intensity) is created for the person at a given speed. This can be used to eliminate situations, in which the person should exercise at too high or low a speed relative to their own fitness level and, in addition, limit the length of the exercise to be reasonable.
6. On the basis of the route information, altitude data being available, the achievement of the target is divided intelligently into uphill, downhill, and flat portions of the route, in such a way that the exercise is appropriate at every stage of the route. For example, on downhill segments there is no need to reach the target as much as on flat ground and so the intensity can be lower. By the same logic, on uphill segments it is preferable to reach the target slightly earlier, i.e. the intensity must be slightly higher than on flat ground. A target speed, for example, can be calculated for each route segment, taking the person's physiological capacity (maximum oxygen uptake), form of exercise, and the route gradient profile into account (see FIG. 12).
7. During the exercise, the user's external work output, physiological response to the work output in question (e.g., heart rate), and physiological state relative to reaching the target on the set route (Cumulative quantities) are monitored. If, for example, due to weather or other conditions, or changes in physical fitness or performance technique, the target is reached considerably more slowly or quickly relative to the route, the allocation of time to the target on the route is readjusted, or if necessary the route is completely readjusted.
8. During the workout, the user is given feedback, on the basis of which the intensity or speed are adjusted in such a way that the target will be reached when the distance/route ends.
9. During the workout, the target or distance/route can be reset. In this case, the operations of Section 5 are performed and the workout can continue.
10. The distance/route ends and the target is reached within the framework of the distance/route.

When planning the route, a preset work form (e.g., running, cycling, etc.) can be exploited. For example, when the target is a specific amount of energy consumption, a downhill portion can be assumed to be taken at a reasonable speed on a bicycle, but a corresponding amount of energy will not consumed.

Distance/route applications can be implemented using the following: heart rate monitors or other devices measuring heart rate, personal digital assistant (PDA) devices, mobile terminals, navigators, and other similar devices, which can be carried by the user during exercise. In addition, the route database can be located on a PC or be a server-based internet service. Positioning data can be collected and monitored using a GPS device, as can altitude data. In addition, the altitude data can be measured on the basis of variations in air pressure, either alone, or combined with GPS altitude data. An application that takes the gradient profile of a pre-selected route into account comprises one or more of the following in connection with the apparatus of FIG. 10: a GPS receiver or other positioning device (telephone positioning), an atmospheric-pressure sensor, and an acceleration sensor. Program means will also be required for recording the route data and for processing it on the basis of the sensor/positioning data received. As such, dynamic route guidance of this kind is useful and inventive even without the aforementioned expansion of the intensity guidance, though the methods complement each other.

In one embodiment (FIG. 11), the distance/route can be generated automatically to suit the set target, using a target (Sections 1 and 2 of the diagram), a route database (Section 3 of the diagram), and background data on the person (Section 4 of the diagram). For example, a specific distance/route can be selected automatically initially on the basis of a specific energy-consumption target.

In one embodiment, a physiological target and distance are set, in which case during the exercise the duration of the exercise changes dynamically depending on the speed. The exercise is guided, however, in such a way that the set physiological target will be reached at the end of the workout when the distance has been completed.

In one embodiment, the system initially plans the route beforehand on the basis of certain assumptions made about the form of work and the user's background data (Section 5 of the diagram) and, as the route progresses, account is taken of the user's physiological state relative to their progress along the route. Thus, for example, when skiing and the snow conditions are slower or faster and the physiological stress response correspondingly greater or smaller, the existing route can be re-planned, in such a way that the target will be reached. If it is no longer possible to reach the physiological target, the system can propose an alternative longer/more demanding route. Alternatively, a shorter/easier route may have to be proposed, if it appears that the physiological target will be exceeded. For example, it may be necessary to advise the user to shorten or lengthen the route started, if the conditions are indeed poorer or better than the default values.

In one embodiment of the invention, the user's warming up and cooling down are taken into account in the allocation/initial planning of the route, during which time the target need not be reached so strongly.

Practical Example 1

In one embodiment of the invention a specific training-effect target and a specific distance target are set. The application of the distance/training effect target pair is shown in FIG. 13 and is reviewed in the text below according to the numbered stages shown in the figure:

1. The user sets the training-effect target and the distance or route target. In the system depicted, a specific training-effect target always corresponds to a specific EPOC value, which can either be displayed to the user, or be only known to the system.
2. The user starts the workout, during which the speed is measured and the intensity estimated. The intensity can be calculated with the aid of heart rate, speed, or some other variable, for example, the pedaling power measured from the pedals of a bicycle.
3. When the time, distance traveled, and speed at a specific moment are known, it is possible to estimate how much time must still elapse to travel the distance set as the target. If the profile of the route is known, the fact that in uphills distance will be covered slower than on the flat, or correspondingly that in downhills distance will be covered faster than on the flat, can be taken into account. Thus, on the basis of heart rate or speed the oxygen or energy consumption or MET values (the ratio of present oxygen consumption to resting oxygen consumption) are estimated and the time of the coming specific route is calculated using present oxygen or energy consumption, or using the MET reading.
4. Once it is known how much time the remaining distance/route will take, an estimate is made as to whether the present intensity will accumulate sufficient peak EPOC for the peak value before the distance target is reached.
5. If the distance and training-effect targets are estimated to be reached sufficiently simultaneously, 'suitable pace' feedback is given.
6. If the intensity is too low, 'increase pace' feedback is given. If the intensity is too high, 'reduce pace' feedback is given.

In this case, as in all other embodiments of the invention, the feedback given can be visual or auditive, or it can be implemented by other means, for example, using various vibration alarms.

Figure 13:
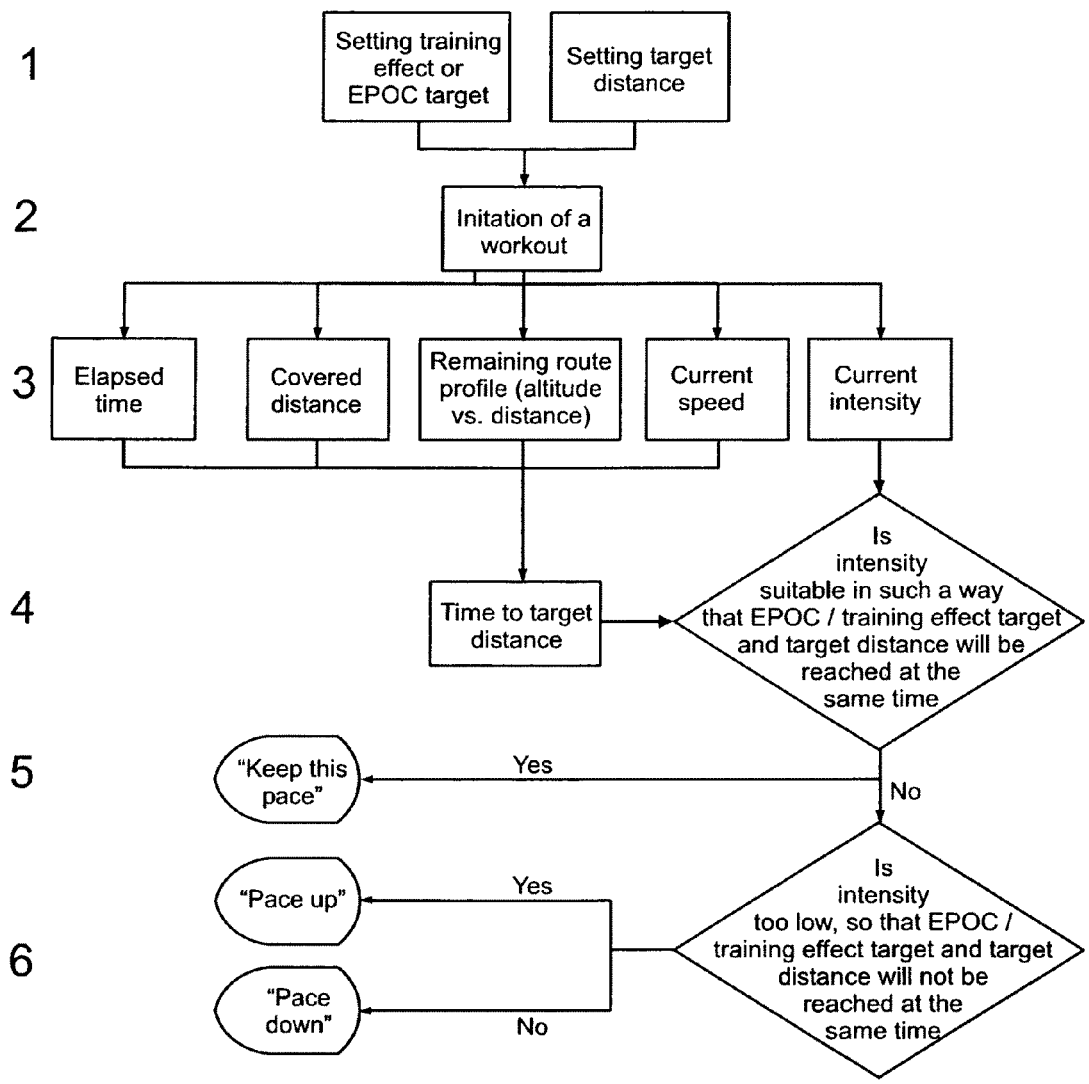
FIG. 13 shows a flow diagram of one detailed embodiment of the invention.

The example shown in FIG. 13 is simplified, for example, in terms of the operation of the system and does not show all the stages. The dynamic exercise guidance system described above can also be exploited in the target setting based on trip described here. The dynamically changing 'time to distance target' will then replace the fixed target time.

In one embodiment of the invention, there can be simultaneously more than one two targets, one of which must always be either the distance or the route. The additional targets can be one or more of the following: time, a given EPOC accumulation, cumulative energy consumption, a given external work, mean intensity, mean heart rate, or similar. Naturally the system should then eliminate impossible target combinations.

In one embodiment of the invention, the target can be to perforin a target distance or route in a target time. The speed guidance on the route is not only based on the calculation of a target speed, but instead the target route is divided into separate segments, which have different target speeds, depending on how easy/difficult the terrain is or depending on the profile (uphill, downhill) (=stress profile). In addition to different target-speed setting for uphill and downhill segments, the exercise is guided dynamically in such a way that a small variation is permitted in the intensity. If for example, the user is behind the target, the target speed increases, or if the user is ahead of the target the target speed decreases.

Practical Example 2

Initial data: a heart rate measuring device is available, which can also measure the distance traveled/speed in real time during the exercise. The altitude data is not known beforehand, so that it cannot be utilized in the intelligent planning of the route. The user wishes to make a developing workout (training effect 3.5) over their usual loop route, the length of which (8.3 km) the user knows already. Description: the user sets the training effect target to 3.5 and the distance target to 8.3 km. on the device and starts running. From the device/earphones the user is informed if the present pace is suitable, too fast or too slow relative to reaching the training-effect target in the target distance. During the first third of the workout, the pace is slightly too fast, so that the user is given feedback showing that the target would be reached at 5 km. The device advises the user to decrease the intensity slightly. For the remainder of the workout the user decreases the intensity slightly to conform to the feedback and the training effect target is reached finally in the target distance.

If speed/distance data are available, but altitude data in any form is not, the user can select from the device's interface whether they are going up or downhill. On uphill segments the physiological target is allowed to be reached slightly faster (higher intensity) and on downhill segments correspondingly slower (lower intensity), relative to the distance traveled.

Practical Example 3

Initial data: a heart rate measuring device, which can also measure the distance traveled/speed in real time during the exercise, is available. The route, over which the user wishes to make a developing workout (training-effect 3.5), is known along with its altitude data. The first quarter (¼) of the route is flat, the second quarter (²⁄₄) uphill, the third quarter (¾) downhill, and the fourth quarter (⁴⁄₄) flat.

The user uploads the route data to the device and sets the training effect target as 3.5. Because the beginning of exercise is relative flat, the accumulated training effect in this portion of the route is less than in the uphill segment. On the uphill segment a higher intensity is permitted and thus more training effect is accumulated. This pleases the user, as it is pleasant to run quickly in uphill and not being required to reduce speed to walking pace. On the downhill segment, the intensity is guided to be pleasantly slightly lower and training effect is barely accumulated so there is no need to run fast in the downhill. This is pleasant for the user, as their legs are subject to smaller impacts. On the final flat segment the intensity is again guided to be slightly higher than on the downhill segment, so that the training effect also reaches the target value of 3.5 at the end of the route.

In one embodiment of the invention, the user selects not only the target distance or target time, but also one or more of the following targets: training effect, EPOC, energy consumption, oxygen consumption, mean heart rate, mean intensity, mean speed, amount of work, mean power of external work, blood lactic acid concentration, target time. In one embodiment of the invention, the user defines one or more physiological target states and a time target. After this, the system plans a suitable route, in which both the physiological target states and the time target will be reached within the desired time tolerances. In planning, the system takes into account, for example, the altitude profile of the route or the ease/difficulty of the terrain (generally the stress profile). If the system selects a route, it utilizes in the route selection data on the target and target distance and the user's physical fitness and/or performance ability (e.g., VO2max). The system checks the selections and does not begin route planning if it detects the user's physical fitness to be such that the user could not reach the target on any route.

In one embodiment of the invention, the system can make proposals to change a pre-selected route, if the system detects that the physical state at the moment of the end of the exercise will remain less than the target, or exceed it. In this case, the system either shortens the route or selects an easier route.

In one embodiment of the invention, data on the performance ability of the user is exploited to define the absolute lower limit of the intensity guidance range. FIGS. 16a and 16b show the relevant lower limit to the expansion of the intensity guidance range. In this case, the target state is some EPOC value, or a training-effect value. The user is thus guided to move at a higher intensity always when the difference between the present and target EPOC is lower as a function of the distance/time than the value defined in the accompanying figures. Naturally, the limits can differ and can include not only a direct fitness level (e.g., the user's VO2max), but in addition or instead also take into account the person's training history. Correspondingly, the limits can be defined for any other cumulative physiological target state whatever, for instance, for energy consumption. At its simplest, information on the user's performance ability is required when applying the invention using only a target distance-target time pair.

The limits shown in FIGS. 16a and 16b can be exploited already when setting the exercise targets, i.e. not to permit the user to set an EPOC or training-effect target (or other cumulative physiological target), that the user could not reach during the remaining time or distance.

In one embodiment of the invention, the upper limit of the expansion of the intensity range is defined in such a way that, during the exercise and before the target time/distance has been reached, a reasonable predetermined portion of the physiological target must be left for the user to be accumulated during the remainder of exercise. For example, at the start of the exercise, the user is not permitted to get too close to the target state, so that the remainder of the exercise will not be inappropriately easy. Thus, if during the exercise, the user gets too close to the target, relative to the remaining distance or time, they will be advised to reduce intensity.

Practical Example 4

Figure 14A:
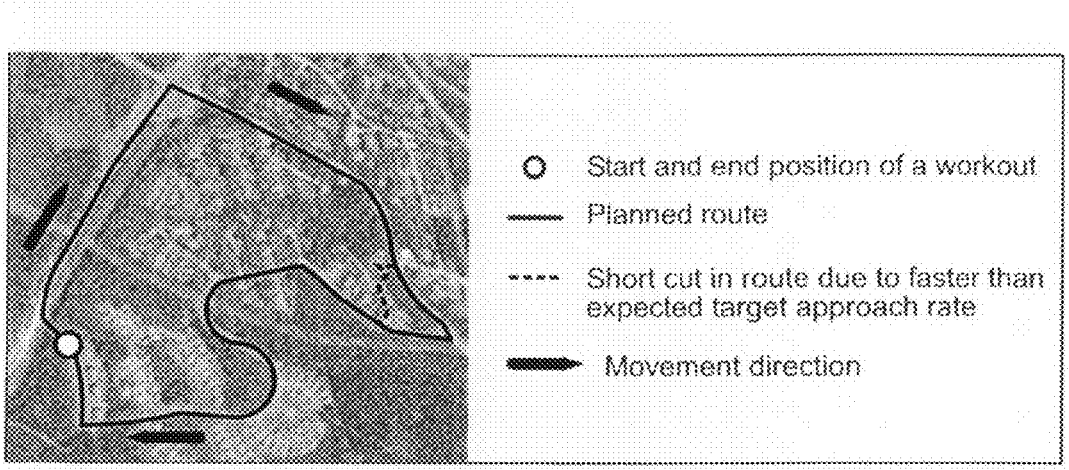
FIGS. 14a and 14b, as well as 15a and 15b show some practical examples of a route-based system.
Figure 14B:
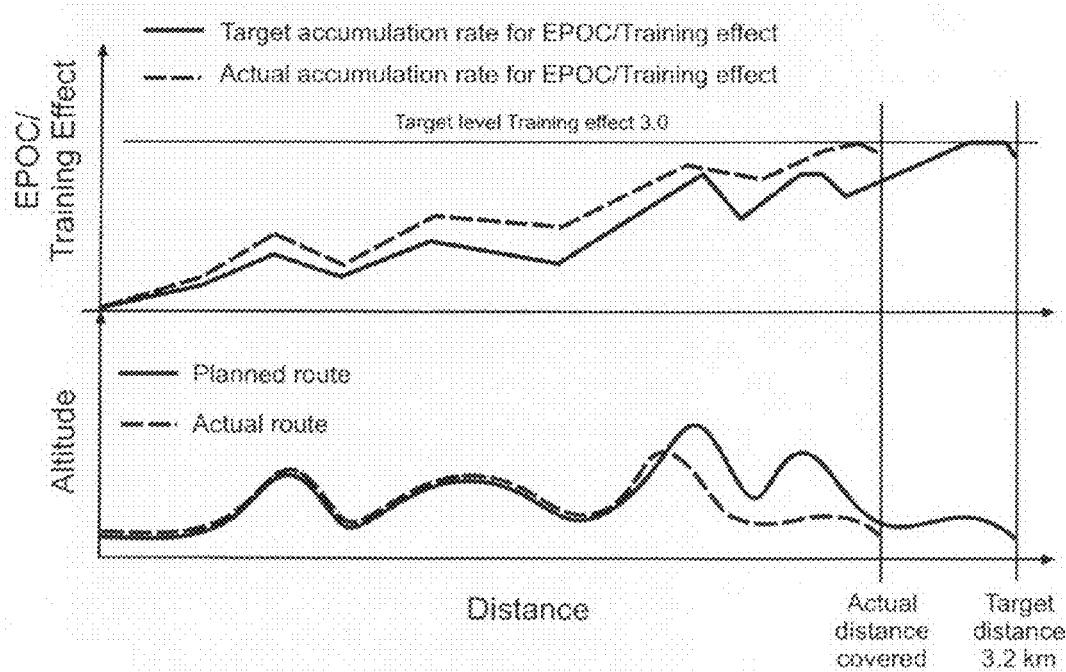

In the example in FIGS. 14a and 14b, the target set is to run around the specific route shown in FIG. 14a, which is 3.2-km. long. The user either selects the route himself/herself, or the system can propose the route if the user has defined the target distance. The target can also be to reach the training effect 3.0 (improving training effect) by running around the route. At the beginning of the route, the intensity is higher than intended and the training effect target is reached faster than intended. The system decides to propose to the user that the route could be shortened (FIG. 15a) and eased by suitably leaving out the steep uphill at the end of the route (FIG. 15b). Thus, the system proposes to the user a short cut, so that the training-effect target will not be exceeded. The user decides to follow the system's proposal and make the short cut and ends the run precisely at the set target (FIG. 15b). However, the user didn't quite reach the distance target (3.2 km.), the real length being 2.7 km. (FIG. 14b). However, the user regards reaching the training-effect target as being more important and the shortening of the route as being of no significance.

In the exercise of the previous example, in addition to distance target a training-effect/EPOC target was also set. The target could also be, for example, a specific fat consumption, energy consumption, blood lactate (lactic acid) concentration at the end of the exercise, or any corresponding cumulative quantity. Of these, EPOC and lactose are, in addition, variables that can also decrease during exercise.

In one embodiment of the invention, all the targets that can be set can be expanded. The expanded targets permit more user-friendly feedback without the system continually interfering with the progress of the exercise. The expansion of the targets takes place within the limits, for example, that the physiological requirements or effects of the exercise will not deviate significantly from its set targets.

Practical Example 5

Figure 15A:
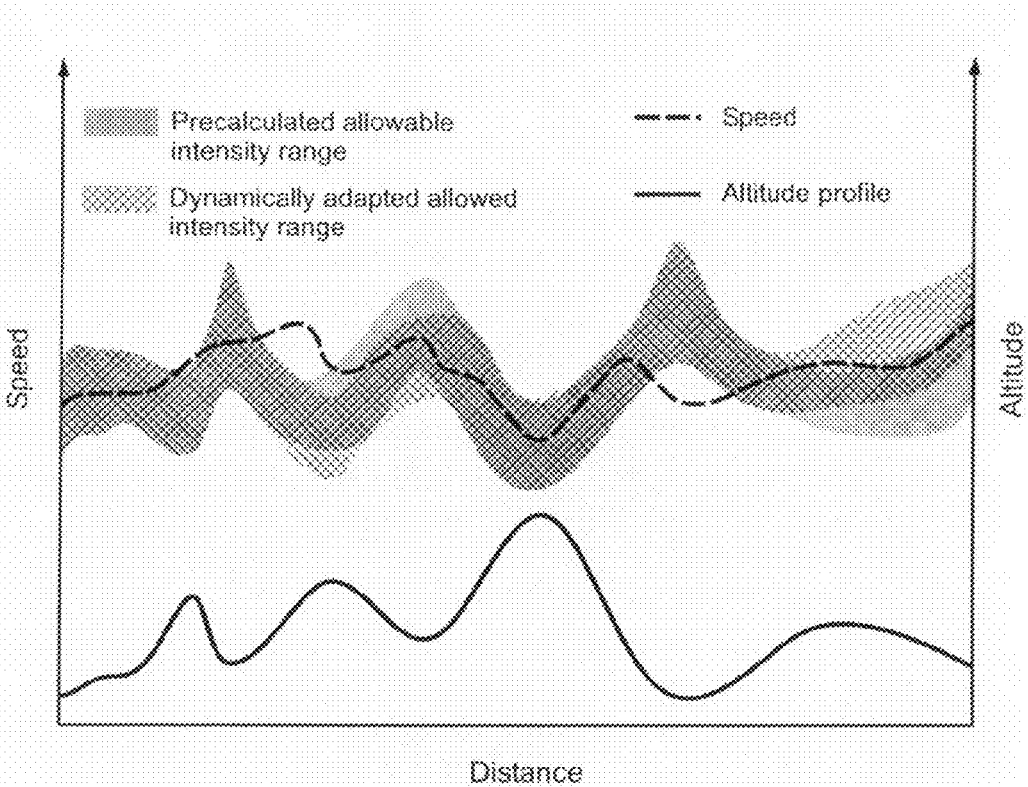
Figure 15B:
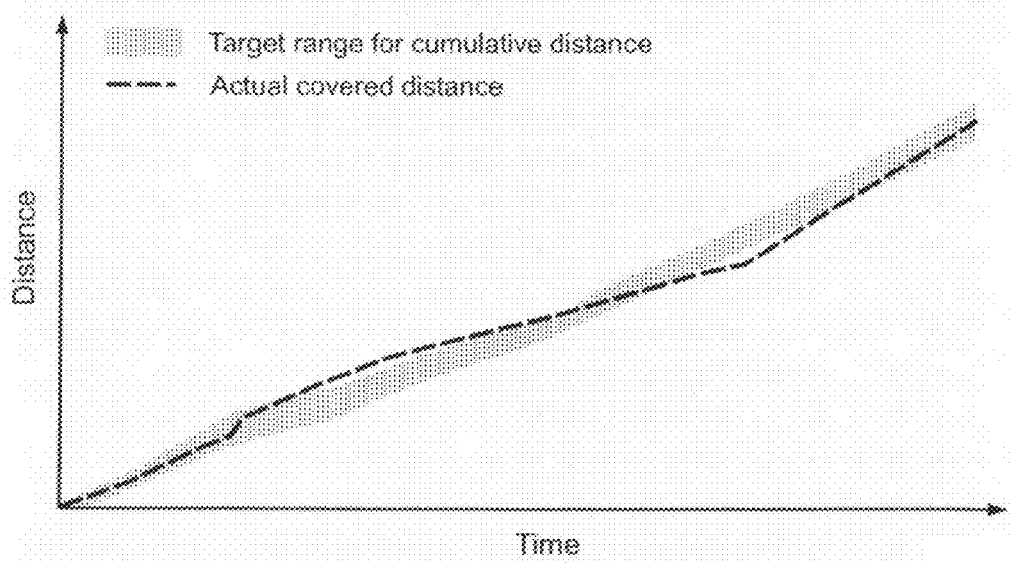

FIGS. 15a and 15b show the progress of exercise when the target set is to travel a target distance in a target time. The route and user's performance ability are known beforehand, so that the system determines the user's optimum speed variation ranges (FIG. 15a). At the start of the exercise, the user moves for some time slightly too quickly, i.e. approaches the distance target slightly too fast (FIG. 15b), so that the predefined target speed variation range is modified slightly downwards (FIG. 15a). Later in the exercise, the user moves for some time slightly too slowly relative to the predefined speed range, so that the speed variation range is dynamically slightly raised. At the end of the exercise, once the target time has elapsed, the user reached the set target distance within the accepted deviation range, which can be, for example, 100 meters. Naturally, a deviation range can be defined for time too, though this is not shown in this example. In the example in question, the intensity guidance system expansions can be included both in a 'time to target' variable as well as in the actual intensity guidance range. The guidance range of intensity guidance range (FIG. 15a) as well as the distance traveled guidance range (FIG. 15b) are in fact expanded. Both lower and upper limits can be defined for the expansions, as stated previously in the present application, in such a way that the exercise can always be performed to the end within the limits of the user's performance ability, and the exercise must always be sensible. Thus, even though the user does not set other targets than time and distance targets, the system can always be permitted to monitor internally that also during the final part of the exercise the EPOC or some other corresponding physiological quantity will still accumulate.

In one embodiment of the invention, the user can select the form of exercise before or while performing the exercise. The forms of exercise that can be selected include the following: running, cycling, skiing, swimming, rowing, kick-sledging, or some other corresponding forms of exercise.

In one embodiment of the invention, there can be several targets, which may require several variation ranges. For example, speed and oxygen consumption (percentage of maximum oxygen consumption VO2max) can simultaneously have their own variation ranges. The different variation ranges can overlap. For example, specific permitted speed-variation ranges can be pre-calculated and are then overlapped with the intensity ranges, so that all criterions are in force simultaneously. Each of the ranges are updated as the exercise progresses. Route data (angles of slope) are exploited when defining the speed-variation range.

In one embodiment of the invention, simple guidance logic can be used to improve guidance when moving downhill. On downhill segments the intensity can be calculated more loosely, because it is not wished to create a situation, in which the speed increases unbearably or unrealistically due to the intensity requirements. It must be accepted that decrease in intensity and increase in speed can occur simultaneously (when on a downhill segment).

In one embodiment of the invention, the EPOC is allowed to decrease in downhill to increase user-friendliness.

In one embodiment of the invention, each part or segment of the route can have its own stress coefficient, by means of which uphill segments, downhill segments, the softness of the ground surface on which the exercise is performed, or other factors relating to the stress effect of the route can be depicted and taken in to account in the dynamic guidance of exercise. In this case, the stress coefficients of the various segments of the route form a stress profile of the route.

Practical Example 6

In one embodiment of the invention, the user sets beforehand as the target achieving a specific EPOC value (which can also be derived from the training effect target) while performing a specific route profile by running/walking. Only the user's position and altitude data are measured, with the aid of a GPS positioning device. The user's maximum oxygen uptake (VO2max) is known. It is either provided by the user, calculated on the basis of the physiological background data provided by the user, or some default value is used.

When the performance is in progress, the user's intensity is observed based on speed and the angle of slope of the route for a specific sampling interval, the EPOC accumulated on the interval in question is calculated, and then added to the already accumulated EPOC. After this, the time that will elapse during the remainder of the route (known profile), if the present intensity is maintained, is calculated. Once the present intensity and the remaining time are known, a prediction of the EPOC accumulating during the remainder of the route can be calculated and, if the already accumulated EPOC is added to this, a prediction of the EPOC accumulated at the end of the route can be calculated.

The varying 'time to target' value, derived from the intensity, speed, and route data is used to return the calculation to a condition where there are only target EPOC and target time. All the rest of the rules, which are depicted as relating to the dynamic guidance, are then in force, guiding the user to the distance and EPOC targets (FIGS. 1, 2, 3, 5, and 6). However, the possibility to exceed the target time should then be limited, because it signifies directly exceeding the target distance. Reaching the EPOC target before the distance target can, however, be permitted, in order to produce a broader intensity width. The user is not shown the estimated time for reaching the target (time to target), but this parameter is determined only to simplify calculations.

In one embodiment of the invention, the user sets a physiological target state and a target distance. The user's speed and altitude (angle of ascent/descent) are measured with the aid of GPS positioning and possibly barometric measurement or by combining acceleration measurement with barometric measurement. The user's background data, etc. are known as in the previous example, but neither the remainder of the route, nor the route as a whole are known. In this case, the remainder of the route is assumed to be on average flat, even though this slightly reduces accuracy. This gives the estimated time for the remainder of the exercise (time to target), as in the previous example, and the user is guided on the basis of this towards the target. Though the gradient profile may not be known in its entirety, in one embodiment of the invention it is possible to utilize information on only the difference in altitude between the starting and finishing points of the exercise. These data can be used to make the intensity guidance more accurate when performing the set distance. In one embodiment, the altitude profile is recorded when travelling over the route for the first time. This requires that the apparatus has, in addition, some kind of altitude-difference meter, positioning means, and a corresponding program.

The invention claimed is:

1. System for guiding a person, with the aid of feedback, to a physiological cumulative state during a physical exercise that is proportional to a change in general homeostatic state achieved by exercising, the physical exercise having
   a duration,
   an intensity that may vary over the duration of the physical exercise and that at any given moment during the physical exercise has a value defined as a momentary intensity,
   a physiological target that is a physiological state of the person at the end of the physical exercise, and
   a performance parameter that is one selected from a group consisting of distance, duration of the exercise, speed, power output of work, EPOC change, accumulated EPOC, energy consumption, energy consumed, oxygen consumption, total oxygen consumption, heart-rate level, TRIMP already accumulated, number of steps, work output as a function of speed and inclination of surface, and change in blood lactic acid concentration,
   the system comprising:
   a sensor for measuring at least one quantity that is proportional to the momentary intensity and selected from a group consisting of heart rate, speed, pedaling power measured from pedals of a bicycle, % $VO_2$max and rate of EPOC accumulation;
   means for recording values of the physiological target and the performance parameter;
   means for giving feedback to the person to keep the exercise intensity within a dynamic intensity guidance range;
   program means for, at regular intervals during the physical exercise:
     recording the measured quantity and a performed physical intensity profile;
     calculating a present physiological state of the person and an estimate of the physiological state at the end of the physical exercise using said measured quantity and the performed intensity profile; and
     defining the intensity guidance range for the momentary intensity so that the physiological target and the performance parameter can be reached within the duration of the physical exercise, the intensity guidance range being defined by calculating a minimum intensity and a maximum intensity required to reach the physiological target and, if the difference between the minimum intensity and the maximum intensity is less than a value according to a preset criteria, the intensity guidance range is expanded by lowering the minimum intensity to a lower value that is equal to the maximum intensity minus the value, whereby the intensity guidance range is expanded during the beginning of the duration of the exercise;

an altimeter; and means for recording and processing route data when an altitude profile is included in the route data, and the program means being arranged to take into account the said altitude profile.

2. System according to claim 1, characterized in that the system includes means for positioning the person and recording and processing route data, and program means for selecting a route to reach the physiological target.

3. System for guiding a person, with the aid of feedback, to a physiological cumulative state during a physical exercise and being proportional to a change in general homeostatic state achieved by exercising, the physical exercise having a duration, an intensity that may vary over the duration of the physical exercise and that at any given moment during the physical exercise has a value defined as a momentary intensity, a physiological target that is a physiological state of the person at the end of the physical exercise, and a performance parameter that is one selected from a group consisting of distance, duration of the exercise, speed, power output of work, EPOC change, accumulated EPOC, energy consumption, energy consumed, oxygen consumption, total oxygen consumption, heart-rate level, TRIMP already accumulated, number of steps, work output as a function of speed and inclination of surface, and change in blood lactic acid concentration, the system comprising:

a sensor for measuring at least one quantity that is proportional to the momentary intensity and selected from a group consisting of heart rate, speed, pedaling power measured from pedals of a bicycle, % $VO_2$max and rate of EPOC accumulation means for recording values of the physiological target and the performance parameter;

means for giving feedback to the person to keep the exercise intensity within a dynamic intensity guidance range; and program means for, at regular intervals during the physical exercise:

recording the measured quantity and a performed physical intensity profile;

calculating a present physiological state of the person and an estimate of the physiological state at the end of the physical exercise using said measured quantity and the performed intensity profile; and defining the intensity guidance range for the momentary intensity so that the physiological target and the performance parameter can be reached within the duration of the physical exercise, the intensity guidance range being defined by calculating a minimum intensity and a maximum intensity required to reach the physiological target and, if the difference between the minimum intensity and the maximum intensity is less than a value according to a preset criteria, the intensity guidance range is expanded by lowering the minimum intensity to a lower value that is equal to the maximum intensity minus the value, whereby the intensity guidance range is expanded during the beginning of the duration of the exercise;

characterized in that the value according to the preset criteria is 30% of maximum intensity.

* * * * *